(12) United States Patent
Wang et al.

(10) Patent No.: US 10,580,125 B2
(45) Date of Patent: *Mar. 3, 2020

(54) METHODS, DEVICES, AND SYSTEMS FOR IMPROVED QUALITY INSPECTION OF PRODUCTS

(71) Applicant: MIDEA GROUP CO., LTD., Foshan (CN)

(72) Inventors: Dongyan Wang, San Jose, CA (US); Haisong Gu, Cupertino, CA (US); Tao Liu, Sunnyvale, CA (US)

(73) Assignee: MIDEA GROUP CO., LTD., Foshan (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/293,417

(22) Filed: Mar. 5, 2019

(65) Prior Publication Data

US 2019/0206045 A1    Jul. 4, 2019

Related U.S. Application Data

(63) Continuation of application No. 15/694,115, filed on Sep. 1, 2017, now Pat. No. 10,269,108.

(51) Int. Cl.
*G06T 7/00* (2017.01)
*B25J 9/16* (2006.01)
(Continued)

(52) U.S. Cl.
CPC ........... *G06T 7/0004* (2013.01); *B25J 9/1697* (2013.01); *G01N 21/9515* (2013.01);
(Continued)

(58) Field of Classification Search
CPC ....... B25J 9/1674; B25J 9/1697; G01B 11/30; G01N 21/88; G01N 21/9515;
(Continued)

(56) References Cited

U.S. PATENT DOCUMENTS

| | | | |
|---|---|---|---|
| 6,959,108 B1 * | 10/2005 | Bartelt | G06T 7/0004 348/125 |
| 7,395,606 B2 * | 7/2008 | Crampton | B25J 13/088 33/503 |

(Continued)

OTHER PUBLICATIONS

Wang, Notice of Allowance, U.S. Appl. No. 15/694,115, dated Dec. 31, 2018, 9 pgs.

*Primary Examiner* — Yon J Couso
(74) *Attorney, Agent, or Firm* — Morgan, Lewis & Bockius LLP

(57) ABSTRACT

A method of quality inspection is performed by a robotic arm that includes a plurality of segments, a camera at an end of the robotic arm, and a plurality of joints connecting two segments of the plurality of segments. The method includes (i) inspecting, via the camera, a surface of a product with the camera positioned at a first position, (ii) based on the inspecting, identifying: (a) an area of interest on the surface of the product, and (b) a relative location of the area of interest on the surface, (iii) positioning, based on the relative location of the area of interest on the surface, the camera at a second position, and (iv) inspecting, via the camera, the area of interest on the surface of the product with the camera positioned at the second position. Inspecting the area of interest includes inspecting a subset of the surface of the product.

19 Claims, 10 Drawing Sheets

(51) Int. Cl.
  *G01N 21/95* (2006.01)
  *G01N 21/88* (2006.01)
  *G01B 11/30* (2006.01)

(52) U.S. Cl.
  CPC ............ *G06T 7/001* (2013.01); *B25J 9/1674* (2013.01); *G01B 11/30* (2013.01); *G01N 21/88* (2013.01); *G01N 2021/8861* (2013.01); *G01N 2021/8887* (2013.01); *G01N 2021/9518* (2013.01); *G06T 2207/20021* (2013.01); *G06T 2207/30108* (2013.01)

(58) Field of Classification Search
  CPC ... G01N 2021/8861; G01N 2021/8887; G01N 2021/9518; G06T 7/0004; G06T 7/001; G06T 2207/20021; G06T 2207/30108
  See application file for complete search history.

(56) References Cited

U.S. PATENT DOCUMENTS

| | | | |
|---|---|---|---|
| 8,240,726 B2* | 8/2012 | Subotincic | B25J 15/0052 294/65 |
| 2008/0140321 A1* | 6/2008 | Blanc | B25J 9/1674 702/41 |
| 2012/0093422 A1* | 4/2012 | Hsu | G06T 7/001 382/218 |
| 2016/0084633 A1* | 3/2016 | Ferrari | G01B 21/04 33/503 |
| 2016/0125583 A1* | 5/2016 | Amanullah | G06T 7/001 348/87 |
| 2017/0205378 A1* | 7/2017 | Sarr | G01N 29/2487 |

* cited by examiner

600

| Defect Pixel 602-A | | | |
|---|---|---|---|
| | ... | | |
| | | ... | |
| | | | Defect Pixel 602-N |

| Defect Pixel 602-A | | | |
|---|---|---|---|
| | ... | | |
| | | ... | |
| | | | Defect Pixel 602-N |
| 604 | | | |

METHODS, DEVICES, AND SYSTEMS FOR IMPROVED QUALITY INSPECTION OF PRODUCTS

RELATED APPLICATIONS

This application is a continuation of U.S. patent application Ser. No. 15/694,115 filed Sep. 1, 2017, entitled "Methods and Systems for Improved Quality Inspection of Products using a Robot," which is hereby incorporated by reference in its entirety.

TECHNICAL FIELD

This relates generally to production lines, including but not limited to visually inspecting products on production lines.

BACKGROUND

Manufacturers implement various quality control measures to reduce an amount of defective products entering the stream of commerce. Some quality control measures involve visually inspecting products. However, current visual inspection techniques, such as visual inspections by human workers, invariably miss defective products and also lack procedures to account for new product defects (e.g., product defects caused by an aging production line). As such, challenges exist in initially identifying product defects, especially product defects that develop over time.

SUMMARY

Accordingly, there is a need for methods and systems for identifying defective products before the defective products enter the stream of commerce. One solution to the problem is using a robot (e.g., a robotic arm 402 with a camera 408 mounted on an end of the robotic arm 402, FIG. 4A) to visual inspect a product prior to the product entering the stream of commerce. In doing so, the robot can examine relevant surfaces and/or features of the product (or in some situations, each surface and/or feature of the product). Moreover, if the robot identifies an abnormality during an initial inspection of the product (e.g., an image captured by the robot includes an abnormality, such as a product defect), the robot is capable of performing a more exacting inspection of the product (e.g., reposition itself to focus on the abnormality). In this way, a manufacturer is able to further reduce an amount of defective products entering the stream of commerce by leveraging the precision and accuracy of a robot and also the processing power of a computer associated with the robot. Additionally, the robot can create a defect database for each identified defect, which it can then use to identify defects on future products. A method of operating one such robot is described below.

(A1) In some implementations, a method of improved quality inspection includes, at a robotic arm (e.g., robotic arm 300, FIG. 3; robotic arm 402, FIG. 4A) having a plurality of segments, a camera at an end of the robotic arm, a plurality of rotatable joints, each rotatable joint connecting two segments of the plurality of segments or the camera with one segment of the plurality of segments, one or more processors, and memory storing instructions for execution by the processors, (i) receiving a command to capture a first image of a surface of a product, (ii) positioning, by actuating the plurality of rotatable joints, the camera at a first position that is substantially adjacent to the surface of the product, and capturing, via the camera, the first image of the surface of the product with the camera positioned at the first position. The method further includes, after capturing the first image: (i) processing the first image to identify a defect in the first image and a relative location of the defect in the first image, and (ii) determining a second position of the camera in accordance with the first position of the camera and the relative location of the defect in the first image, and (iii) repositioning, by actuating the plurality of rotatable joints, the camera from the first position to the second position. The second position has a different spatial relationship to the surface of the product than the first position. The method further includes capturing, via the camera, the second image of the surface of the product with the camera positioned at the second position.

(A2) In some implementations of the method of A1, the camera is separated from the surface by a first distance when positioned at the first position, the camera is separated from the surface by a second distance when repositioned at the second position, and the second distance is less than the first distance.

(A3) In some implementations of the method of any of A1-A2, the camera is set at a first focal length when positioned at the first position, the camera is set at a second focal length when repositioned at the second position, and the second focal length is greater than the first focal length.

(A4) In some implementations of the method of any of A1-A3, the method further includes determining a size of the product from the first image of the surface of the product and the first position of the camera, and based on the determined size, assigning a working space for the robotic arm. The size may include one or more of the product's height, width, length, and volume. In some implementations, the working space for the robotic arm is further determined based on a configuration of the robotic arm. For example, a robotic arm having a first configuration (e.g., robotic arm 402, FIG. 4A) may be assigned a first working space (e.g., using a first working space equation) and a robotic arm having a second configuration (e.g., robotic arm 440, FIG. 4C) may be assigned a second working space (e.g., using a second working space equation).

(A5) In some implementations of the method of any of A1-A4, positioning the camera at the first position and repositioning the camera from the first position to the second position is performed within the working space determined for the robotic arm.

(A6) In some implementations of the method of any of A1-A5, the plurality of rotatable joints provides the robotic arm with four degrees of freedom (e.g., the robotic arm 402 has, at least in some implementations, four degrees of freedom).

(A7) In some implementations of the method of any of A1-A5, the plurality of rotatable joints provides the robotic arm with five degrees of freedom (e.g., the robotic arm 420 has, at least in some implementations, five degrees of freedom).

(A8) In some implementations of the method of any of A1-A7, a first set of rotatable joints in the plurality of rotatable joints rotate about a first axis, and a second set of rotatable joints in the plurality of rotatable joints rotate about a second axis.

(A9) In some implementations of the method of any of A1-A8, the first set of rotatable joints is body rotatable joints (e.g., rotatable joints 406-B and 406-C, FIG. 4A), and the second set of rotatable joints is end rotatable joints (e.g., rotatable joints 406-A and 406-D, FIG. 4A).

(A10) In some implementations of the method of any of A1-A9, the method further includes: (i) repositioning, by actuating the plurality of rotatable joints, the camera at one or more additional positions, each additional position is substantially adjacent to a respective additional surface of the product, and (ii) capturing, via the camera, an additional image of each respective additional surface of the product with the camera positioned at the one or more additional positions.

(A11) In some implementations of the method of any of A1-A10, the product is positioned on a rotatable base (e.g., rotatable base 410, FIG. 4A). Moreover, the method further includes, after capturing the first image, rotating the rotatable base in accordance with the relative location of the defect in the first image. The second image is captured after rotating the rotatable base.

(A12) In another aspect, a robotic arm is provided (e.g., robotic arm 300, FIG. 3). The robotic arm includes a plurality of segments, a camera at an end of the robotic arm, a plurality of rotatable joints, each rotatable joint connecting two segments of the plurality of segments or the camera with one segment of the plurality of segments, one or more processors, and memory storing one or more programs, which when executed by the one or more processors cause the robotic arm to perform the method described in any one of A1-A11.

(A13) In yet another aspect, a robotic arm is provided and the robotic arm includes means for performing the method described in any one of A1-A11.

(A14) In still another aspect, a non-transitory computer-readable storage medium is provided. The non-transitory computer-readable storage medium stores executable instructions that, when executed by a robotic arm (e.g., robotic arm 300, FIG. 3) with one or more processors/cores, cause the robotic arm to perform the method described in any one of A1-A11.

BRIEF DESCRIPTION OF THE DRAWINGS

For a better understanding of the various described implementations, reference should be made to the Description of Implementations below, in conjunction with the following drawings in which like reference numerals refer to corresponding parts throughout the figures and specification.

FIGS. 6A-6B show a defect model and a new defect being added to the defect model, in accordance with some implementations.

DESCRIPTION OF IMPLEMENTATIONS

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

It will also be understood that, although the terms first, second, etc. are, in some instances, used herein to describe various elements, these elements should not be limited by these terms. These terms are used only to distinguish one element from another. For example, a first image could be termed a second image, and, similarly, a second image could be termed a first image, without departing from the scope of the various described implementations. The first image and the second image are both images, but they are not the same images.

The terminology used in the description of the various described implementations herein is for the purpose of describing particular implementations only and is not intended to be limiting. As used in the description of the various described implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting" or "in accordance with a determination that," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]" or "in accordance with a determination that [a stated condition or event] is detected," depending on the context.

As used herein, the term "exemplary" is used in the sense of "serving as an example, instance, or illustration" and not in the sense of "representing the best of its kind."

Figure 1:
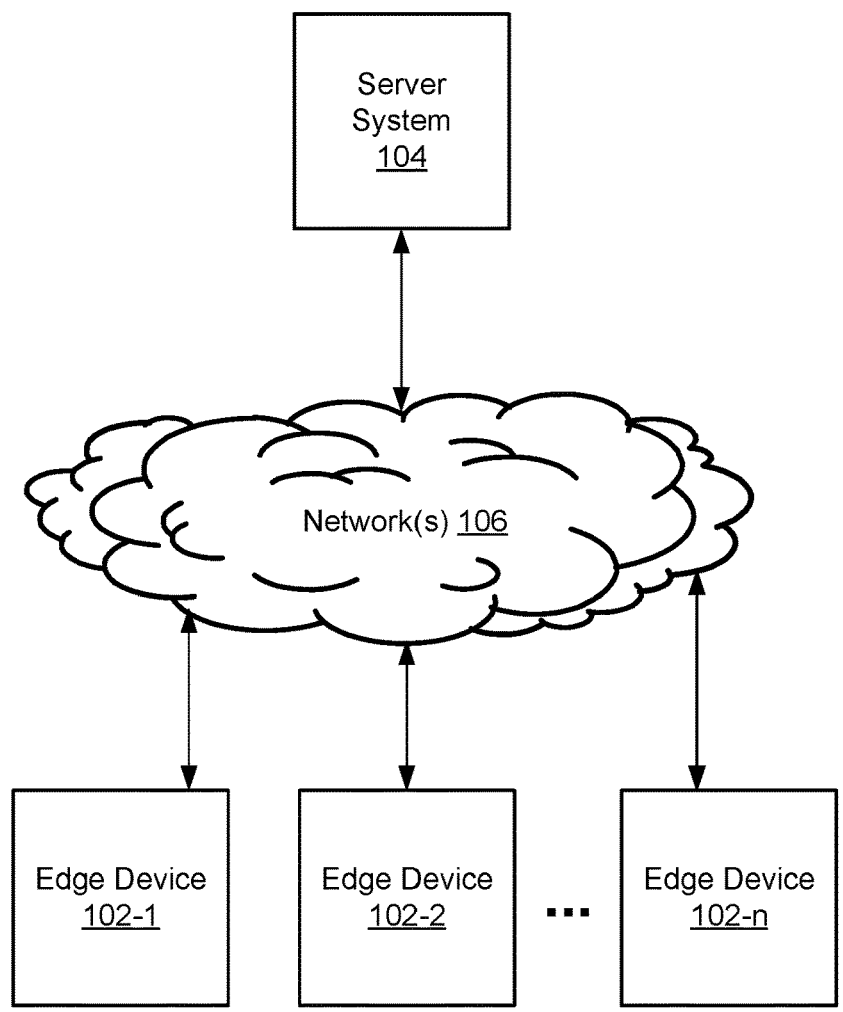
FIG. 1 is a block diagram illustrating an exemplary network architecture of a product inspection network, in accordance with some implementations.

FIG. 1 is a block diagram illustrating an exemplary network architecture 100 of a product inspection network, in accordance with some implementations. The network architecture 100 includes a number of edge devices 102-1, 102-2, . . . 102-n communicably connected to a server system 104 by one or more networks 106.

In some implementations, the edge devices 102-1, 102-2, . . . 102-n are electronic devices that can communicate with the server system 104, each other, and other devices. In some implementations, the server system 104 is a single computing device such as a computer server, while in other implementations, the server system 104 is implemented by multiple computing devices working together to perform the actions of a server system (e.g., cloud computing). In some implementations, the server system 104 is at one (or each) of the edge devices 102-1, 102-2, . . . 102-n. In such implementations, the server system 104 is a computer at the respective edge device (i.e., the server system 104 is a local computer and/or is part of the respective edge device). In some implementations, the network 106 is a public communication network (e.g., the Internet or a cellular data network), a private communications network (e.g., private LAN or leased lines), or a combination of such communication networks.

The edge devices 102-1, 102-2, . . . 102-n are used to inspect (e.g., monitor) products. In some implementations, the edge devices 102-1, 102-2, . . . 102-n monitor an operation's effect on a product (e.g., perform quality control). To do this, each of the edge devices 102-1, 102-2, . . . 102-n includes one or more capture devices, such as a camera, an infrared camera, an X-ray camera, a depth camera, etc. The goal being that the edge devices 102-1, 102-2, . . . 102-n identify product defects or collect data that can be used to identify product defects.

Figure 4A:
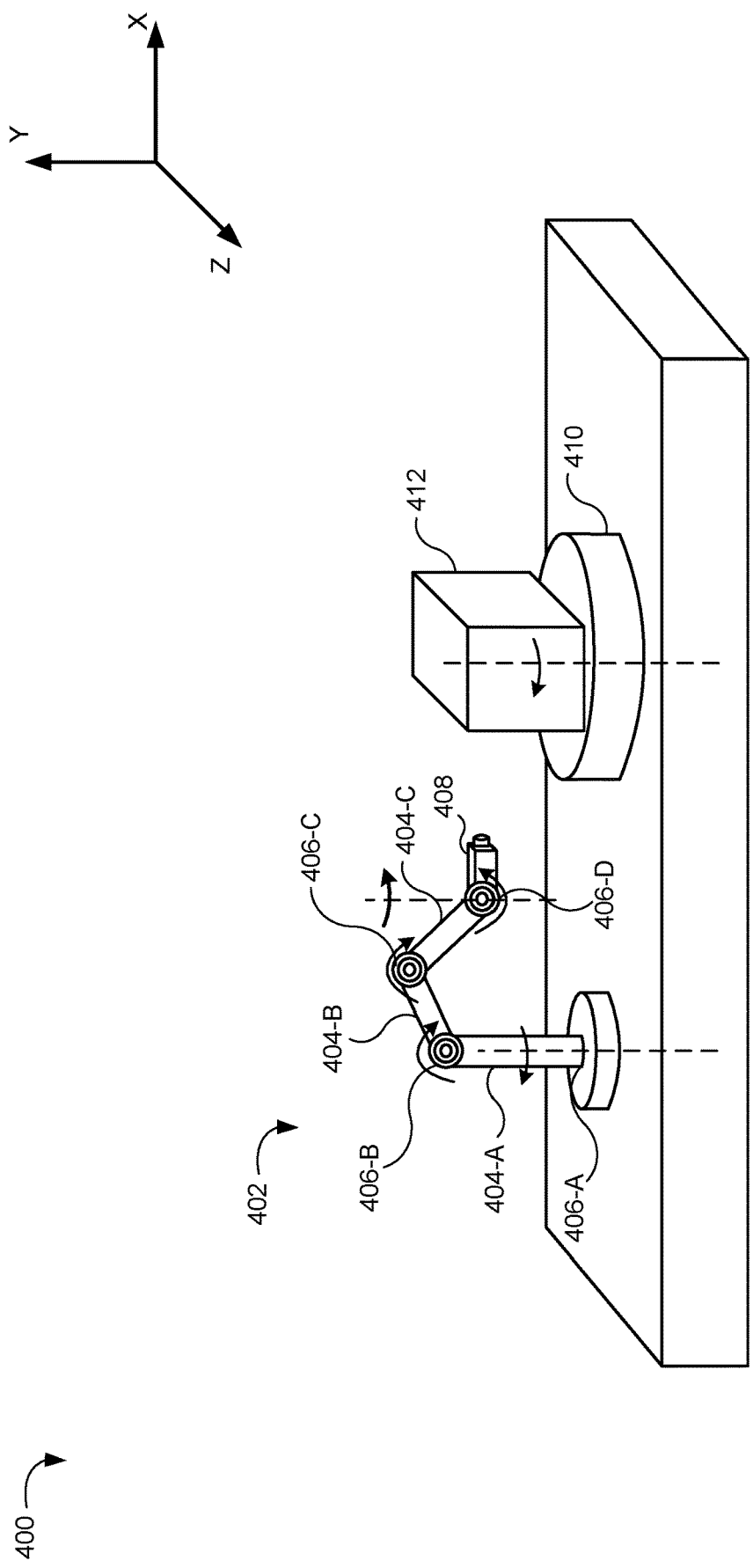
FIG. 4A is an exemplary robotic arm that is used to inspect a product, in accordance with some implementations.

In some implementations, an edge device 102 is a robotic arm with a camera attached to an end of the robotic arm (e.g., robotic arm 402, FIG. 4A). Although multiple edge devices are shown in FIG. 1, in some implementations, a single edge device is in communication with the server system 104.

In some implementations, the edge devices 102-1, 102-2, . . . 102-n send the captured data to the server system 104. The server system 104 can then use the received data to evaluate a product for product defects. Alternatively, in some implementations, the edge devices 102-1, 102-2, . . . 102-n evaluate a product for product defects locally (e.g., in those implementations where the server system 104 is a computer at the edges devices 102-1, 102-2, . . . 102-n).

Figure 2:
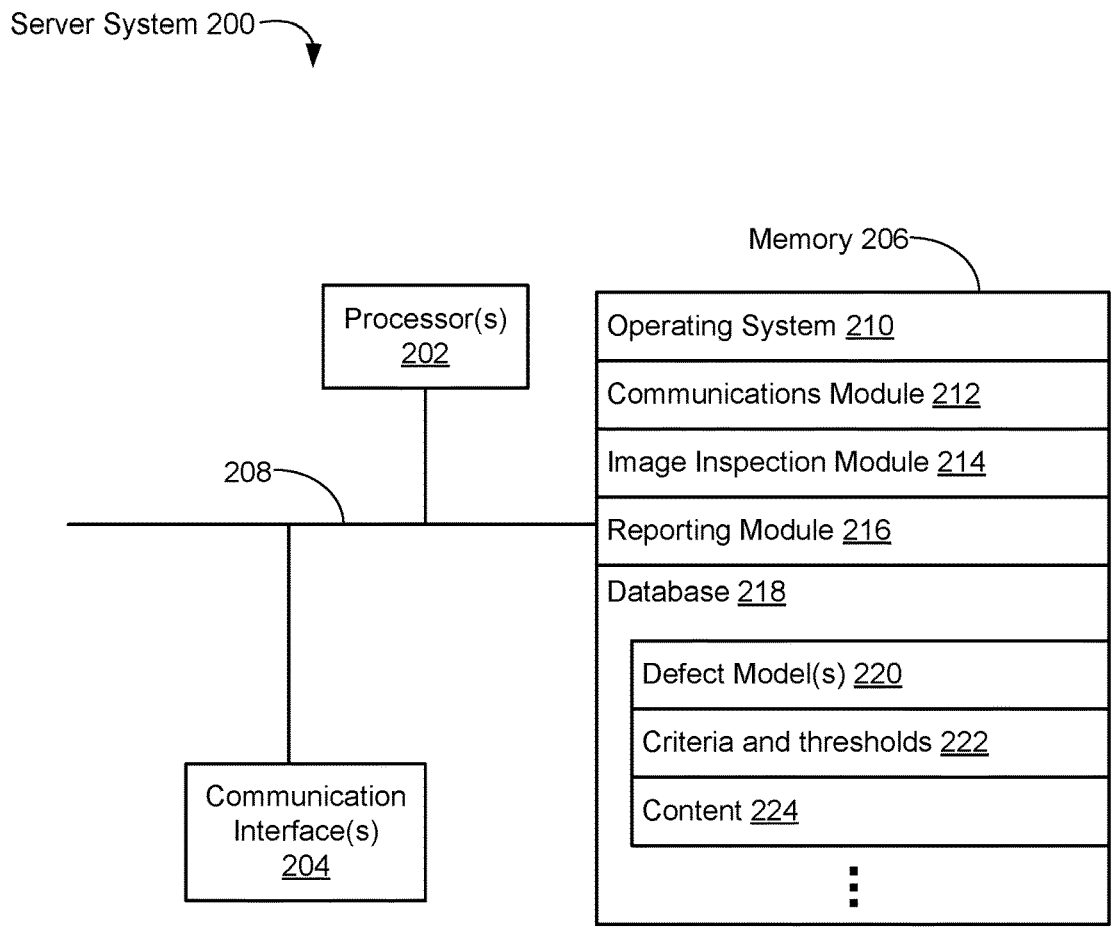
FIG. 2 is a block diagram illustrating an exemplary server system, in accordance with some implementations.

FIG. 2 is a block diagram illustrating an exemplary server system 200 in accordance with some implementations. In some implementations, the server system 200 is an example of a server system 104 (FIG. 1). As noted above, in some implementations, the server system 104 is distinct and separate from the edge devices 102-1, 102-2, . . . 102-n. Alternatively, in some implementations, the server system 104 is part of the edge devices 102-1, 102-2, . . . 102-n (or part of a respective edge device).

The server system 200 typically includes one or more processing units (processors or cores) 202, one or more network or other communications interfaces 204, memory 206, and one or more communication buses 208 for interconnecting these components. The communication buses 208 optionally include circuitry (sometimes called a chipset) that interconnects and controls communications between system components. The server system 200 optionally includes a user interface (not shown). The user interface, if provided, may include a display device and optionally includes inputs such as a keyboard, mouse, trackpad, and/or input buttons. Alternatively or in addition, the display device includes a touch-sensitive surface, in which case the display is a touch-sensitive display.

Memory 206 includes high-speed random access memory, such as DRAM, SRAM, DDR RAM, or other random access solid state memory devices; and may include non-volatile memory, such as one or more magnetic disk storage devices, optical disk storage devices, flash memory devices, or other non-volatile solid state storage devices. Memory 206 may optionally include one or more storage devices remotely located from the processor(s) 202. Memory 206, or alternately the non-volatile memory device(s) within memory 206, includes a non-transitory computer readable storage medium. In some implementations, memory 206 or the computer readable storage medium of memory 206 stores the following programs, modules, and data structures, or a subset or superset thereof:

- an operating system 210 that includes procedures for handling various basic system services and for performing hardware-dependent tasks;
- a network communication module 212 that is used for connecting the server system 200 to other computers (e.g., robotic arm 300, FIG. 3) via the one or more communication 204 (wired or wireless) and one or more communication networks 106 (FIG. 1), such as the Internet, cellular telephone networks, mobile data networks, other wide area networks, local area networks, metropolitan area networks, and so on;
- an image inspection module 214 that is used for processing data received from one or more edge devices and that is used for analyzing the processed data. In some implementations, the visual inspection module compares the processed data with defect model(s) 220 (e.g., defect table 600, FIG. 6A);
- a reporting module 216 that is used for recording and reports defects; and
- a server database 218 for storing data associated with the server system, such as:
  one or more defect models 220;
  one or more criteria and thresholds 222; and
  content 224.

In some implementations, the one more defect models 220 include previously identified defects and/or desired results (i.e., non-defect pixels).

The one or more criteria and thresholds 222 can include thresholds for identifying a defect. For example, a threshold difference (or threshold similarity) between a piece of an image captured and a defect pixel included in a defect model 220. Additionally, in some implementations, an image is not deemed to include a defect until a threshold number of pieces of the image are deemed to include defects.

The content 224 can include data received from the robotic arm 300 (FIG. 3), such as images captured by the robotic arm. In some implementations, the content 230 includes text (e.g., ASCII, SGML, HTML), images (e.g., jpeg, tif and gif), graphics (e.g., vector-based or bitmap), audio, video (e.g., mpeg), other multimedia, and/or combinations thereof.

The server database 218 stores data associated with the server system 200 in one or more types of databases, such as text, graph, dimensional, flat, hierarchical, network, object-oriented, relational, and/or XML databases.

In some implementations, the server system 200 stores in memory a graph of the edge devices. For example, the graph identifies each edge device on a particular production line and connections between each edge device. The connections may include a position of the edge device, an orientation of the edge device, neighboring edge devices, etc.

Figure 3:
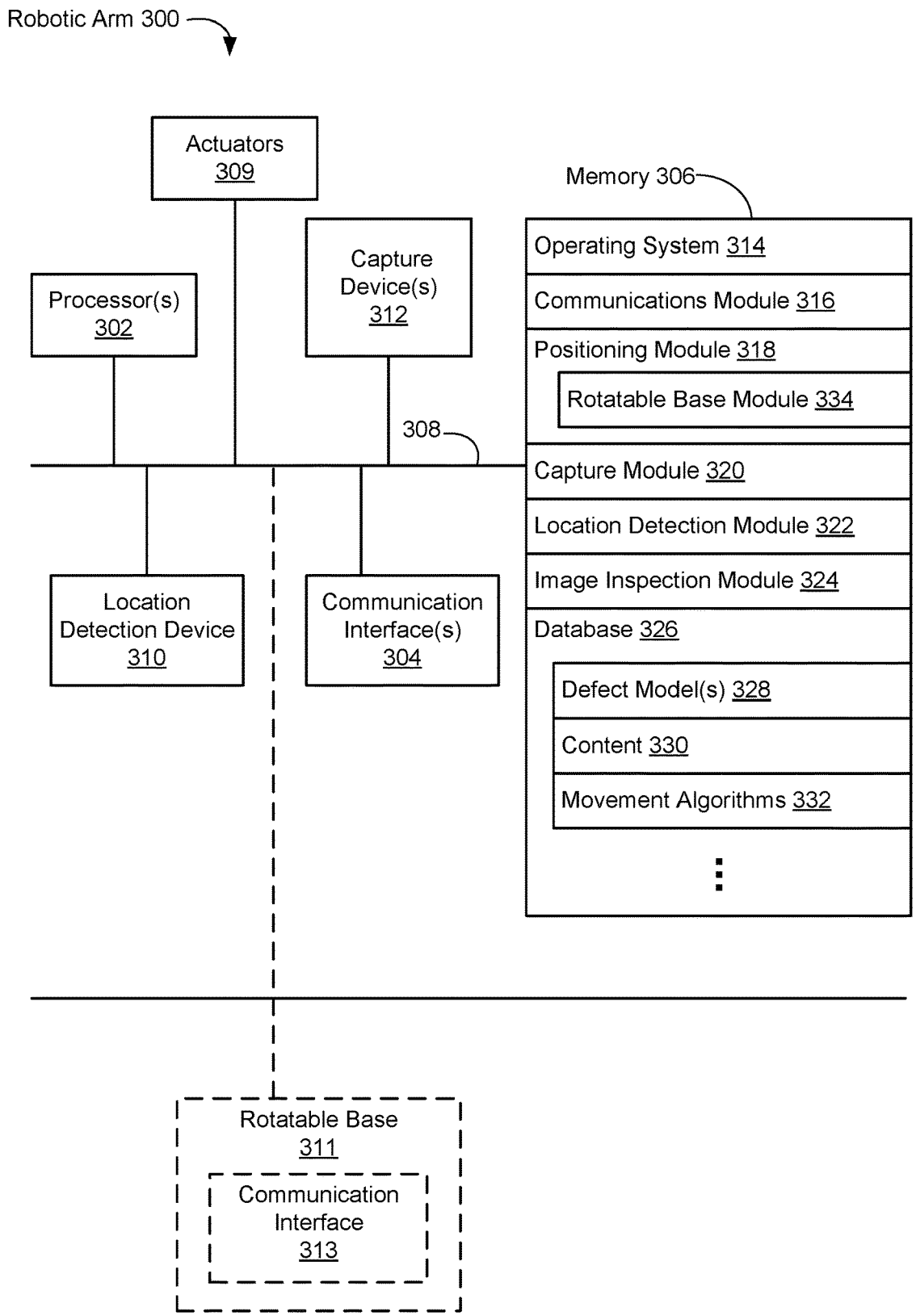
FIG. 3 is a block diagram illustrating an exemplary robotic arm, in accordance with some implementations.

FIG. 3 is a block diagram illustrating an exemplary robotic arm 300, in accordance with some implementations. The robotic arm 300 is an example of one of the one or more edge devices 102-1, 102-2, . . . 102-n (FIG. 1). The robotic arm 300 typically includes one or more processing units (processors or cores) 302, one or more network or other communications interfaces 304, memory 306, one or more communication buses 308 for interconnecting these components, and actuators 309 (e.g., rotatable joints 406-A-406-D, FIG. 4A). The communication buses 308 optionally include circuitry (sometimes called a chipset) that interconnects and controls communications between system components. The robotic arm 300 optionally includes a location detection device 310, such as a GNSS (e.g., GPS, GLONASS, etc.) or other geo-location receiver, for determining the location of the robotic arm 300. The robotic arm 300 also includes one or more capture devices 312, such as a camera, an infrared camera, an X-ray camera, a depth camera, a three-dimensional camera, and the like.

In some implementations, the robotic arm 300 includes one or more optional sensors (e.g., gyroscope, accelerometer) for detecting motion and/or a change in orientation of the robotic arm 300. In some implementations, the detected motion and/or orientation of the robotic arm 300 is used during positioning of the robotic arm 300, or to indicate that the robotic arm 300 requires adjusting or realigning.

In some implementations, the robotic arm 300 includes, or controls, a rotatable base 311 (e.g., rotatable base 410, FIG. 4A). In some implementations, the robotic arm 300 communicates with the rotatable base 311 via the one or more communication buses 308. Alternatively, in some implementations, the robotic arm 300 communicates with the rotatable base 311 via communication interface(s) 304 and communication interface 313, respectively. In some implementations, the server system 200 controls the rotatable base 311.

Memory 306 includes high-speed random-access memory, such as DRAM, SRAM, DDR RAM, or other random-access solid-state memory devices; and may include non-volatile memory, such as one or more magnetic disk storage devices, optical disk storage devices, flash memory devices, or other non-volatile solid-state storage devices. Memory 306 may optionally include one or more storage devices remotely located from the processor(s) 306. Memory 306, or alternately the non-volatile memory device(s) within memory 306, includes a non-transitory computer-readable storage medium. In some implementations, memory 306 or the computer-readable storage medium of memory 306 stores the following programs, modules, and data structures, or a subset or superset thereof:
- an operating system 314 that includes procedures for handling various basic system services and for performing hardware-dependent tasks;
- a network communication module 316 that is used for connecting the robotic arm 300 to other computers (e.g., other edge devices, the server system 200, the rotatable base 311) via the one or more communication network interfaces 304 (wired or wireless) and the one or more communication networks 106 (FIG. 1), such as the Internet, cellular telephone networks, mobile data networks, other wide area networks, local area networks, metropolitan area networks, and so on;
- a positioning module 318 that is used for controlling the actuators 309 and positioning a capture device 312 in proximity to a product;
- a capture module 320 that is used for controlling the capture device(s) 312 and processing a respective image or video (or other data) captured by the capture device(s) 312;
- a location detection module 322 (e.g., a GPS, Wi-Fi, or hybrid positioning module) that is used for determining the location of the robotic arm 300 (e.g., using the location detection device 310) and providing this location information to other edge devices and/or the server system 200;
- an image inspection module 324 that is used for detecting product defects using data captured by the capture devices 312; and
- a database 326 for storing data associated with the robotic arm 300, such as:
  - one or more defect models 328;
  - content 330; and
  - movement algorithms and other equations 332.

In some implementations, the positioning module 318 includes a rotatable base module 334 that is used for controlling (i.e., rotating) the rotatable base 311. As discussed in more detail below, the rotatable base module 334 rotates the rotatable base 311 according to a location of a defect identified in an image captured by the capture device(s) 312. Moreover, in some implementations, the rotatable base module 334 rotates the rotatable base 311 to an initial position prior to capturing the image (e.g., the first image 500, FIG. 5B).

In some implementations, the one more defect models 328 include previously identified defects and/or desired results (i.e., non-defect pixels). The one or more defect models 328 are discussed in further detail below with reference to FIG. 5B and FIGS. 6A-6B.

In some implementations, the content 330 includes data captured by the capture device(s) 312. In some implementations, the content 334 includes text (e.g., ASCII, SGML, HTML), images (e.g., jpeg, tif and gif), graphics (e.g., vector-based or bitmap), audio, video (e.g., mpeg), other multimedia, and/or combinations thereof. Moreover, in some implementations, the content 330 includes local binary patterns (LBP) generated by the robotic arm 300.

In some implementations, the movement algorithms 332 are forward and inverse kinematic equations. The forward and inverse kinematic equations are used to identify a position of an end effector (or end effectors) of the robotic arm 300 and determine joint parameters that provide a desired position for each of the robotic arm's end-effectors, respectively. The other equations 332 may include working space equations and searching route equations, each of which are described in further detail below.

Each of the above identified modules and applications correspond to a set of executable instructions for performing one or more functions as described above and/or in the methods described in this application (e.g., the computer-implemented methods and other information processing methods described herein). These modules (i.e., sets of instructions) need not be implemented as separate software programs, procedures or modules, and thus various subsets of these modules are, optionally, combined or otherwise re-arranged in various implementations. In some implementations, memory 206 and/or 306 store a subset of the modules and data structures identified above. Furthermore, memory 206 and/or 306 optionally store additional modules and data structures not described above.

Figure 4B:
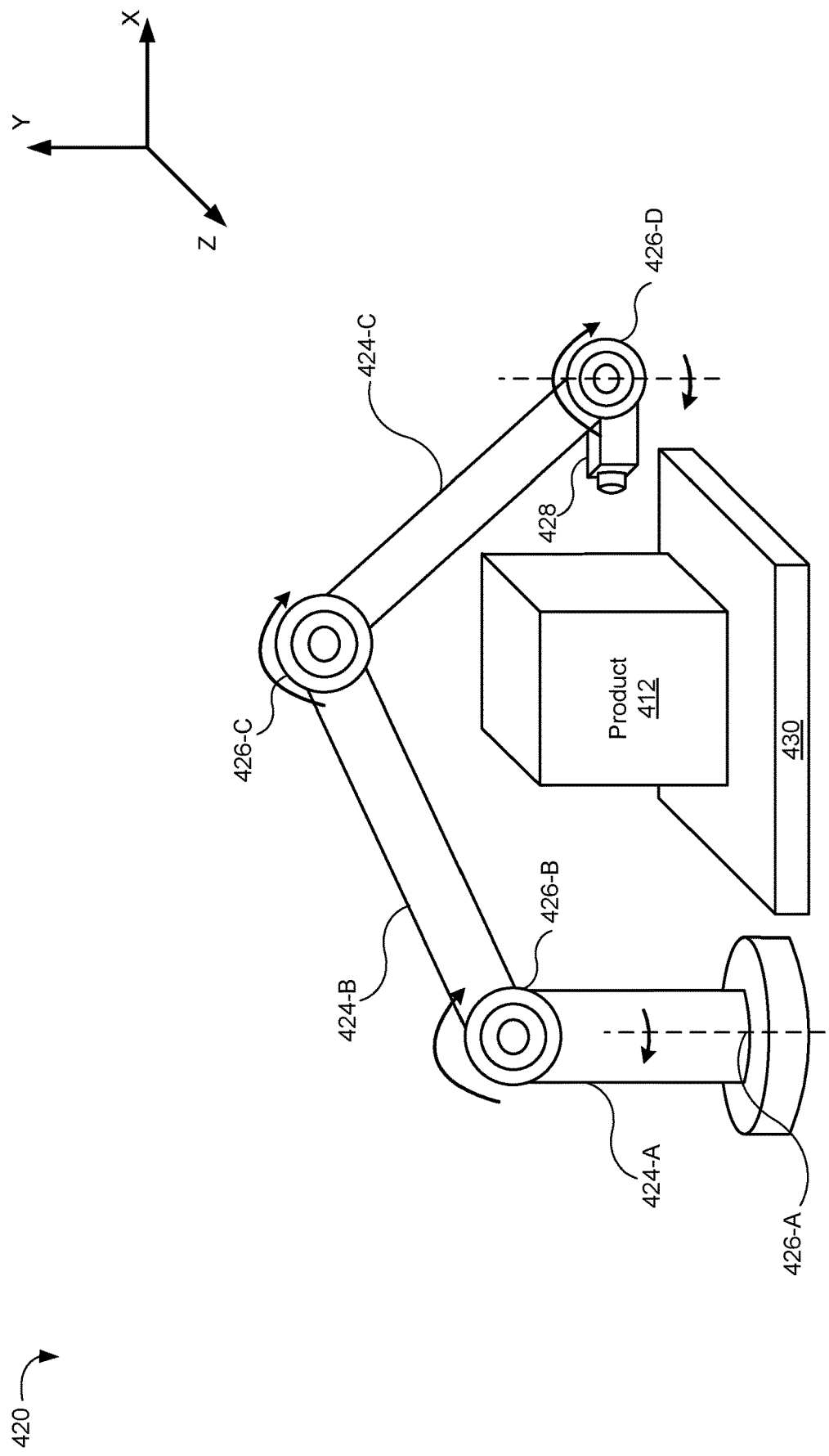
FIG. 4B is an exemplary robotic arm that is used to inspect a product, in accordance with some implementations.
Figure 4C:
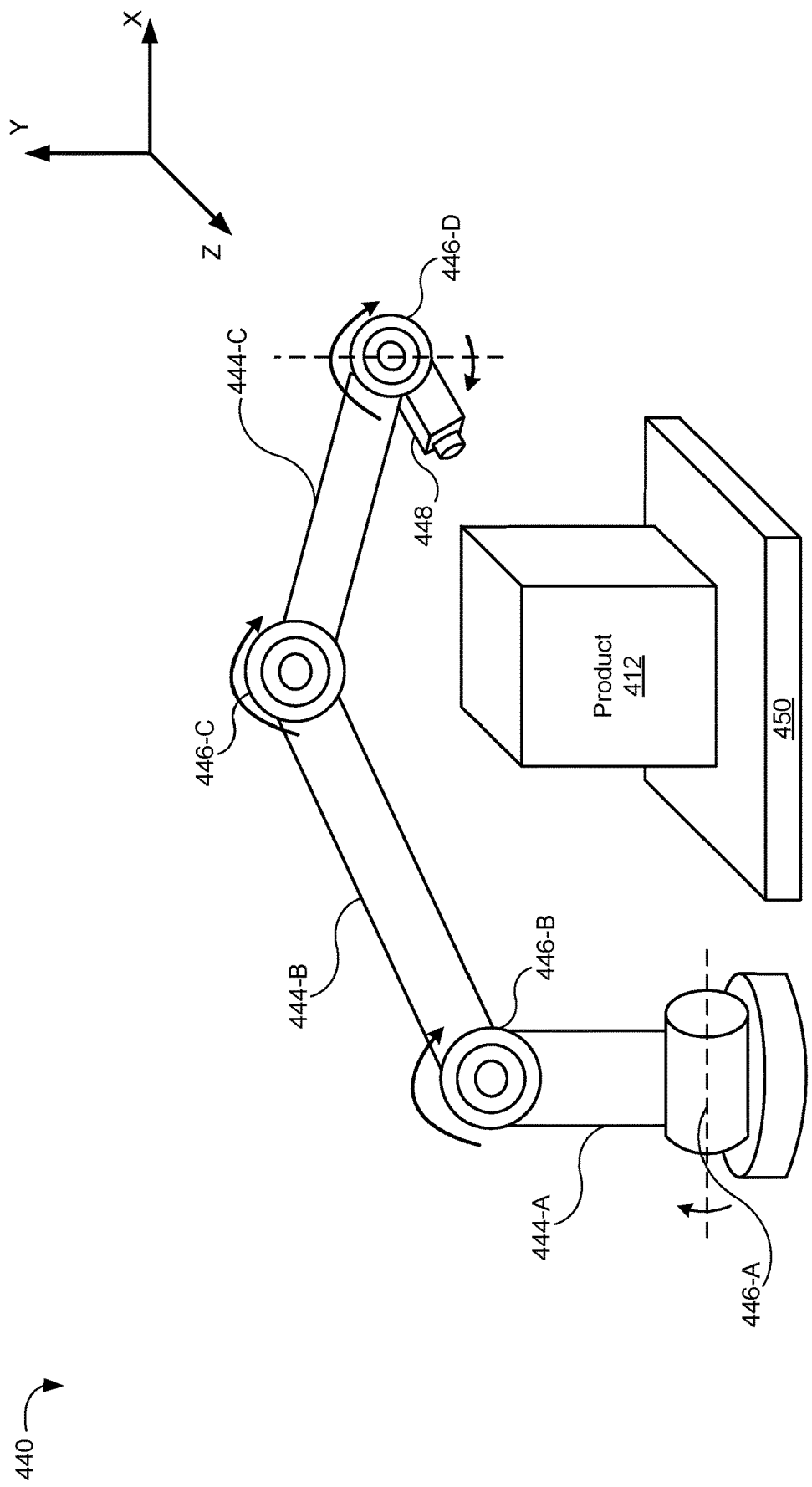
FIG. 4C is an exemplary robotic arm that is used to inspect a product, in accordance with some implementations.

FIGS. 4A-4C show exemplary robotic arms used to inspect products, in accordance with some implementations.

FIG. 4A is an exemplary robotic arm 402 used to inspect a product 412, in accordance with some implementations. As shown, the robotic arm 402 is part of a production line 400, which also includes a rotatable base 410 and a product 412 disposed on top of the rotatable surface 410. The robotic arm 402 is an example of the robotic arm 300 (FIG. 3). It should be noted that the robotic arm 402 can be used to inspect a wide arrange of products, and the product 412 is merely one example.

The robotic arm 402 includes a plurality of segments (or sections) 404-A, 404-B, and 404-C. In some implementations, a length of each of the plurality of segments 404-A, 404-B, and 404-C is substantially the same. Alternatively, in some implementations, a length of at least one segment of the plurality of segments 404-A, 404-B, and 404-C differs from lengths of other segments of the plurality of segments. The lengths shown in FIG. 4A are simply used for illustrative purposes and are not limiting. For example, even though the second segment 404-B is shown to be shorter than the first segment 404-A, in some implementations, the second segment 404-B is longer than the first segment 404-A (the third segment 404-C may also be longer or shorter than the other segments, depending on the circumstances). The robotic arm 402 is shown to include three segments, however, the robotic arm 402 can include various numbers of segments (e.g., two segments, four segments, . . . N-segments).

The robotic arm 402 also includes a plurality of rotatable joints 406-A-406-D (e.g., actuators 309, FIG. 3). In some implementations, a number of rotatable joints included in the plurality of rotatable joints 406-A-406-D corresponds to a number of segments in the plurality of segments 404-A, 404-B, and 404-C (e.g., the number of rotatable joints in the plurality is one greater than the number of the plurality of segments). As shown, the first rotatable joint 406-A rotates about a first axis of rotation (e.g., Y-axis), the second rotatable joint 406-B and the third rotatable joint 406-C rotate about a second axis of rotation (e.g., Z-axis), and the fourth rotatable joint 406-D rotates about one or more of the first axis of rotation and the second axis of rotation. In some implementations, the fourth rotatable joint 406-D also rotates about a third axis of rotation (e.g., X-axis). It should be noted that the rotatable joints can rotate clockwise and/or counterclockwise, and the arrows used in FIGS. 4A-4C should not be construed as limiting a rotatable joints' direction of rotation.

As shown, each rotatable joint 406 connects either: (i) two segments of the plurality of segments 404, or (ii) a camera 408 (discussed below) of the robotic arm 402 with one segment of the plurality of segments 404. In such an arrangement, the robotic arm 402 is composed of substantially contiguous segments.

The robotic arm 402 also includes a camera 408 (e.g., a capture device 312, FIG. 3) attached to an end of the robotic arm. The robotic arm 402 (or a component thereof such as processor(s) 302 or capture module 320, FIG. 3) controls operation of the camera 408. For example, as will be discussed in further detail above, the robotic arm 402 captures an image of the product 412, via the camera 408, after positioning the camera 408 at a desired location. Additionally, in some implementations, the robotic arm 402 controls other features/functions of the camera 408, such as zoom (e.g., the robotic arm 402 adjusts a focal length of the camera 408) and video based features/functions.

In some implementations, the robotic arm 402 positions the camera 408 substantially adjacent to a surface (or feature) of the product 412. Additionally, in some implementations, the robotic arm 402 positions the camera 408 so that the camera 408 is centered about the surface (or the feature) of the product 412. To accomplish this, the robotic arm 402 actuates (e.g., processor(s) 302 and/or positioning module 318) one or more of the plurality of rotatable joints 406-A-406-C. In this way, the camera 408 captures an image of the surface of the product 412, and the robotic arm 402 (or server system 200, FIG. 2) evaluates the image for defects. The robotic arm 402 uses kinematic equations (e.g., forward and/or inverse kinematics) when positioning the camera 408 at a desired location. The kinematic equations are also referred to herein as movement algorithms 332 (FIG. 3).

Moreover, in order to evaluate each surface and/or feature of the product 412, the production line 400 includes a rotatable base 410. In some implementations, the robotic arm 402 (or a component thereof such as the processor(s) 302 or rotatable base module 334, FIG. 3) controls the rotatable base 410. Alternatively, in some implementations, the rotatable base is controlled by some other computing device, e.g., the server system 200 (FIG. 2). Including the rotatable base 410 in the production line 400: (i) allows the robotic arm 402 to evaluate surfaces and/or features of the product 412 with minimal movement, and (ii) reduces a length of each of the plurality of segments 404-A-404-C. For example, the rotatable base 410 rotates the product 412 to present each lateral surface of the product 412 to the camera 408. As such, the robotic arm 402 remains substantially stationary while each lateral surface is placed in front of it (the robotic arm 402 need only reach a top surface of the product 412 as opposed to distant surfaces of the product 412, e.g., as shown in FIGS. 4B-4C).

In some implementations, when positioning the camera 408, the robotic arm 402 considers a field of view of the camera 408. For example, depending on a size of the product being captured, the robotic arm 402 must place the camera 408 at a specific distance away from the product 412 to capture an entire surface of the product 412. This specific distance is dependent on the camera's field of view. An exemplary field of view may be a 60 degree field of view, but other fields of view are possible (e.g., depending on lens type, focal length, camera type, etc.). The field of view ($\beta$) is represented in the working space equations below.

In some implementations, the robotic arm 402 identifies its working space by capturing an initial image of the product 412 (or by evaluating a video feed taken by the camera). For example, in some circumstances, the product 412 is a smaller product, such as a tea kettle, which requires a first working space. However, in some other circumstances, the product 412 is a larger product, such as a refrigerator, which requires a second working space different from the first working space. In some implementations, a working space of the robotic arm 402 is represented by the following equation:

$$l = L + \frac{\max(L, H)}{2\tan\left(\frac{\beta}{2}\right)}$$

$$w = W + \frac{\max(L, H)}{2\tan\left(\frac{\beta}{2}\right)}$$

$$h = H + \frac{\max(L, H)}{2\tan\left(\frac{\beta}{2}\right)}$$

where l, w, and h are the desired working spaces for the robotic arm 402 (e.g., points that an end effector of the robotic arm 402 should reach); L, W, and H are a length, width, and height of the product 412, respectively; and $\beta$ is the field of view of the camera 408. In some implementations, the end effector of the robotic arm 402 is the camera 408. Alternatively, in some implementations, the end effector of the robotic arm 402 is one of the plurality of rotatable joints (or multiple rotatable joints). It should be noted that the rotatable base 410 is factored into the working space equation above. Additionally, working spaces for various products may be stored in memory 306 (FIG. 3) of the robotic arm.

Because the robotic arm 402 is able to identify differences in sizes between products, and the robotic arm 402 is able to position itself accordingly to capture an initial image of the product 412 that is substantially adjacent to and centered about a surface (or feature) of the product 412. In this way, the production line 400 can use a single robotic arm, as opposed to having multiple robotic arms that are calibrated for certain products, thereby lowering an overall cost for the production line 400.

FIG. 4B is an exemplary robotic arm 420 used to inspect a product 412, in accordance with some implementations. The robotic arm 420 is an example of the robotic arm 300 (FIG. 3). One or more features shown and/or described above with reference to FIG. 4A are not described in FIG. 4B for the sake of brevity (or certain features have a shortened description).

The robotic arm 420 includes a plurality of segments (or sections) 424-A, 424-B, and 424-C. In some implementations, a length of each of the plurality of segments 424-A, 424-B, and 424-C is substantially the same. Alternatively, in some implementations, a length of at least one segment of the plurality of segments 424-A, 424-B, and 424-C differs from the other segments of the plurality of segments. Although the robotic arm 420 is shown to include three segments, it should be understood that the robotic arm 420 can include various numbers of segments (e.g., two segments, four segments, . . . N-segments).

The robotic arm 420 also includes a plurality of rotatable joints 426-A-426-D. In some implementations, a number of joints included in the plurality of rotatable joints 426-A-426-D corresponds to a number of segments in the plurality of segments 424-A, 424-B, and 424-C (e.g., the number of joints will be one greater than the number of the plurality of segments). As shown, the first rotatable joint 426-A rotates about a first axis of rotation (e.g., Y-axis), the second rotatable joint 426-B and the third rotatable joint 426-C rotate about a second axis of rotation (e.g., Z-axis), and the fourth rotatable joint 426-D rotates about the first axis of rotation and the second axis of rotation.

As compared to the robotic arm 402 (FIG. 4A), lengths of the plurality segments 424-A-424-C of the robotic arm 420 are substantially greater than lengths of the plurality segments 404-A-404-C of the robotic arm 402. This is because the product 412 is placed on top of a stationary base 430, and therefore, the robotic arm 420 is required to reach each surface of the product 412. As a result of not having the rotatable base 410, the fourth rotatable joint 426-D rotates about the first axis of rotation and the second axis of rotation.

The robotic arm 420 also includes a camera 428 (e.g., capture device 312, FIG. 3) attached to an end of the robotic arm 420. The robotic arm 420 uses the procedures discussed above with reference to FIG. 4A to position the camera 428 substantially adjacent to and centered about a surface (or feature) of the product 412.

In some implementations, the robotic arm 420 identifies its working space by capturing an initial image of the product 412 (or by evaluating a video feed taken by the camera 428). In some implementations, a working space of the robotic arm 420 is represented by the following equation:

$$l = L + \frac{\max(L, H)}{\tan(\beta/2)}$$

$$w = W + \frac{\max(L, H)}{\tan(\beta/2)}$$

$$h = H + \frac{\max(L, H)}{2\tan(\beta/2)}$$

where l, w, and h are the desired working spaces for the robotic arm 420 (e.g., points that an end effector of the robotic arm 420 should reach); L, W, and H are a length, width, and height of the product 412, respectively; and $\beta$ is the field of view of the camera 428. It should be noted that the rotatable base 410 is not part of the working space equation above.

FIG. 4C is an exemplary robotic arm 440 used to inspect a product 412, in accordance with some implementations. The robotic arm 440 is an example of the robotic arm 300 (FIG. 3). One or more features described above with reference to FIG. 4A are not described in FIG. 4C for the sake of brevity (or certain features have a shortened description).

The robotic arm 440 includes a plurality of segments (or sections) 444-A, 444-B, and 444-C. In some implementations, a length of each of the plurality of segments 444-A, 444-B, and 444-C is substantially the same. Alternatively, in some implementations, a length of at least one of the plurality of segments 444-A, 444-B, and 444-C differs from the other segments of the plurality of segments. Although the robotic arm 440 is shown to include three segments, it should be understood that the robotic arm 440 can include various numbers of segments (e.g., two segments, four segments, . . . N-segments).

The robotic arm 440 also includes a plurality of rotatable joints 446-A-446-D. In some implementations, a number of joints included in the plurality of rotatable joints 446-A-446-D corresponds to a number of segments in the plurality of segments 444-A, 444-B, and 444-C (e.g., the number of joints will be one greater than the number of the plurality of segments). As shown, the first rotatable joint 446-A rotates about a first axis of rotation (e.g., X-axis), the second rotatable joint 446-B and the third rotatable joint 446-C rotate about a second axis of rotation (e.g., Z-axis), and the fourth rotatable joint 446-D rotates about one or more of the second axis of rotation and a third axis of rotation (e.g., Y-axis).

The robotic arm 440 also includes a camera 448 (e.g., capture device 312, FIG. 3) attached to an end of the robotic arm. The robotic arm 440 uses the procedures discussed above with reference to FIG. 4A to position the camera 448 substantially adjacent to and centered about a surface (or feature) of the product 412.

As compared to the robotic arm 402 (FIG. 4A), lengths of the plurality segments 444-A-444-C of the robotic arm 440 are substantially greater than lengths of the plurality segments 404-A-404-C of the robotic arm 402. This is because the product 412 is placed on top of a stationary base 450, and therefore, the robotic arm 440 is required to reach each surface of the product 412. However, when compared to the robotic arm 420 (FIG. 4B), the robotic arm 440 is able to capture the five exposed surface of the product 412 with fewer joint actuations than the robotic arm 420. This is accomplished due to the unique joint arrangement of the robotic arm 440 (e.g., the first rotatable joint 446-A rotates about the X-axis, and therefore three surfaces of the product 412 can be captured by actuating the first rotatable joint 446-A).

In some implementations, the robotic arm 440 identifies its working space by capturing an initial image of the product 412 (or by evaluating a video feed taken by the camera 448). In some implementations, a working space of the robotic arm 440 is represented by the following equation:

$$l = L + 4\cos\theta\Delta - \frac{L\sqrt{L^2 + H^2}}{2\sqrt{L^2 + W^2}}$$

$$w = W + 4\cos\theta\Delta - \frac{W\sqrt{L^2 + H^2}}{2\sqrt{L^2 + W^2}}$$

$$h = H + 2\sin\theta\Delta$$

where, $$\theta = \beta - \cos^{-1}\sqrt{\frac{2(L^2 + W^2)}{L^2 + W^2 + 4H^2}}$$

$$\Delta = \sqrt{\left(\frac{L^2 + H^2}{4}\right) + H^2}$$

and where l, w, and h are the desired working spaces for the robotic arm 440 (e.g., points that an end effector of the robotic arm 440 should reach); L, W, and H are a length, width, and height of the product 412, respectively; and β is the field of view of the camera 448. It should be noted that the rotatable base 410 is not part of the working space equation above.

Figure 5A:
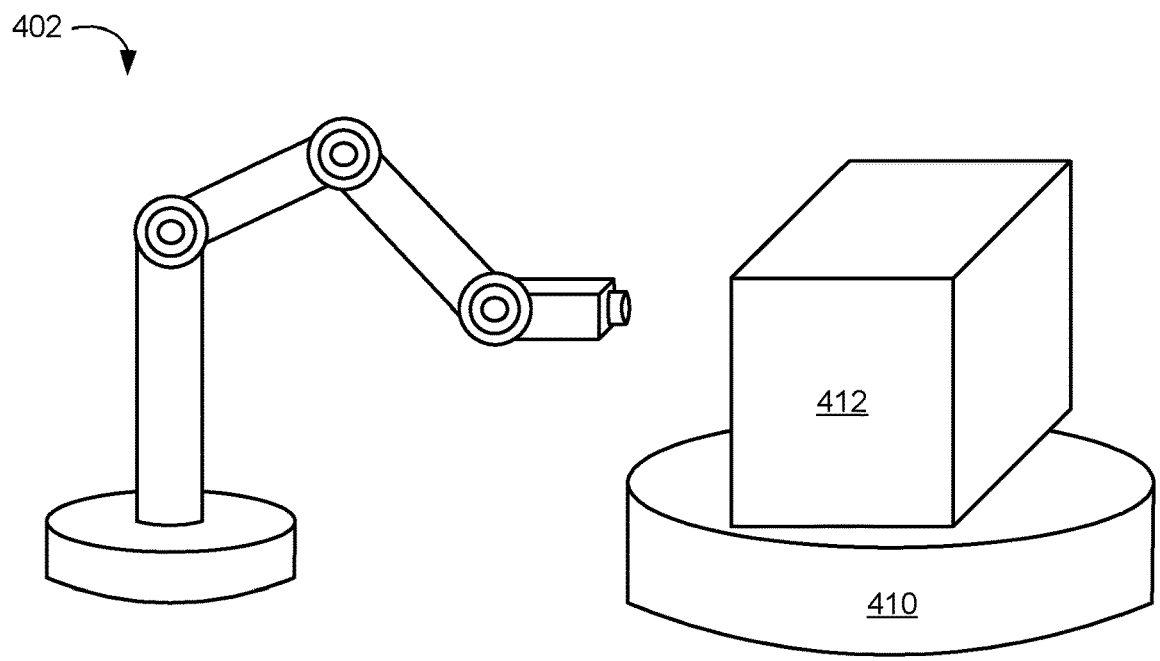
FIGS. 5A-5B show a robotic arm capturing a first image of a product and a resulting image with a defect, in accordance with some implementations.
Figure 5B:
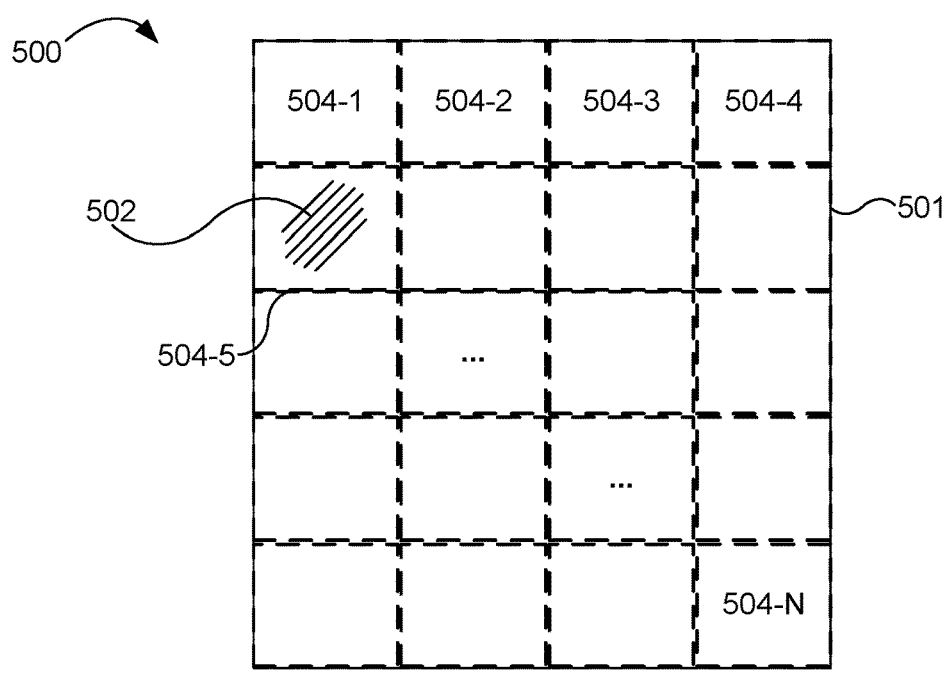

FIGS. 5A-5B show a robotic arm 402 capturing a first image 500 of a product 412, and a result of the capturing, in accordance with some implementations.

As discussed above with reference to FIGS. 4A-4C, the robotic arm 402 (or a component thereof such as the processor(s) 302 or a positioning module 318, FIG. 3) positions the camera 408 so that the camera 408 is substantially adjacent to and centered about a surface (or feature) of the product 412. In some implementations, the robotic arm 402 accomplishes this by first identifying the product 412 to be captured (e.g., microwave oven versus refrigerator), and based on the identified product, the robotic arm 402 determines its working space, which factors in a field of view of the camera 408. Additionally, the robotic arm 402 executes one or more kinematic equations to position itself. In doing so, the robotic arm 402 positions the camera 408 at a sufficient distance away from the surface of the product 412 so that the camera 408 captures an acceptable image (e.g., an image that includes the entire surface, or an entire feature). This arrangement is illustrated in FIG. 5A.

FIG. 5B shows a first image 500 captured by the camera 408. The first image 500 includes the surface 501 of the product 412 captured by the camera 408, and a defect 502 on the surface 501.

In some implementations, the robotic arm 402 (or a component thereof such as the processor(s) 302 or an image inspection module 324, FIG. 3) identifies the defect 502 by processing (e.g., analyzing, evaluating, etc.) the first image 500. In some implementations, processing the first image 500 involves comparing portions (e.g., pieces) of the first image 500 with one or more defect models (e.g., defect model(s) 328, FIG. 3). To accomplish this, the robotic arm 402 divides the first image 500 into pieces 504-1-504-N (e.g., forms a grid, where each piece of the grid has an equal size) and compares at least a subset of the pieces 504-1-504-N with one or more defect models (e.g., defect model 600, FIG. 6A). As shown in FIG. 6A, the defect model 600 includes defect pixels 602-A-602-N. It should be noted that in some implementations, a "defect pixel" is a 1×1 pixel, while in some other implementations, a defect pixel includes multiple pixels (e.g., a 25×25 pixel, a 100×100 pixel, or some greater or lesser number of pixels).

In some implementations, the defect pixels corresponds to the pieces of the first image 500 (e.g., a top left corner of defect model 600 includes defect pixels that correspond to a top left corner of the first image 500). As such, the robotic arm 402 compares a first piece 504-1 of the first image 500 with one or more corresponding defect pixels from a defect model for the surface 501 of the product 412 (e.g., defect pixel 602-A, FIG. 6A). In some implementations, the robotic arm 402 flips the one or more corresponding defect pixels left to right and/or top to bottom, during the comparison. Moreover, in some implementations, the robotic arm 402 rotates the one or more corresponding defect pixels 90 degrees, 180 degrees, and/or 270 degrees during the comparison. In this way, the robotic arm 402 evaluates possible variations of the one or more corresponding defect pixels. It should be noted that "flipping" a defect pixel is not the same as "rotating" a defect pixel (e.g., flipping a defect pixel causes features in the defect pixel to be mirrored in the resulting defect pixel).

In some implementations, the robotic arm 402 compares pieces of the first image 500 with the defect pixels sequentially. For example, piece 504-1 is compared with one or more first corresponding defect pixels, piece 504-2 is compared with one or more second corresponding defect pixels, and so on. Alternatively, the robotic arm 402 compares pieces of the first image 500 with the defect pixels randomly, or pseudo-randomly. In some implementations, the robotic arm 402 performs an initial analysis of the first image 500 to identify any abnormalities in the first image 500. If an abnormality is found, e.g., a bottom right corner of the first image 500 differs from a control surface (discussed below), then the robotic arm 402 compares one or more pieces in the bottom right corner of the first image 500 with one or more corresponding defect pixels. In this way, the robotic arm 402 skips processing other portions of the first image 500 that do not include abnormalities, thus saving time and computing resources.

In some implementations, a defect pixel is a previously identified defect. For example, the previously identified defect may be identified during a testing/calibration phase and/or during previous inspections (e.g., if the product 412 is a microwave oven, defects on surfaces of previously inspected microwave ovens are logged and stored). Alternatively or in addition, in some implementations, a defect pixel is a desired result for each piece of the surface 501 of the product 412 (i.e., a non-defect pixel). For example, during a testing/calibration phase, an image of a control surface of a control product is captured, and each piece of the control surface is logged and stored (the control surface corresponding to the surface 501). Moreover, this process may be repeated for several control products to form the defect models 328 (FIG. 3). In this way, the defect models 328 include a desired result with acceptable tolerances (e.g., a threshold difference from the control surface that is required for an abnormality to be deemed a defect).

Figure 5C:
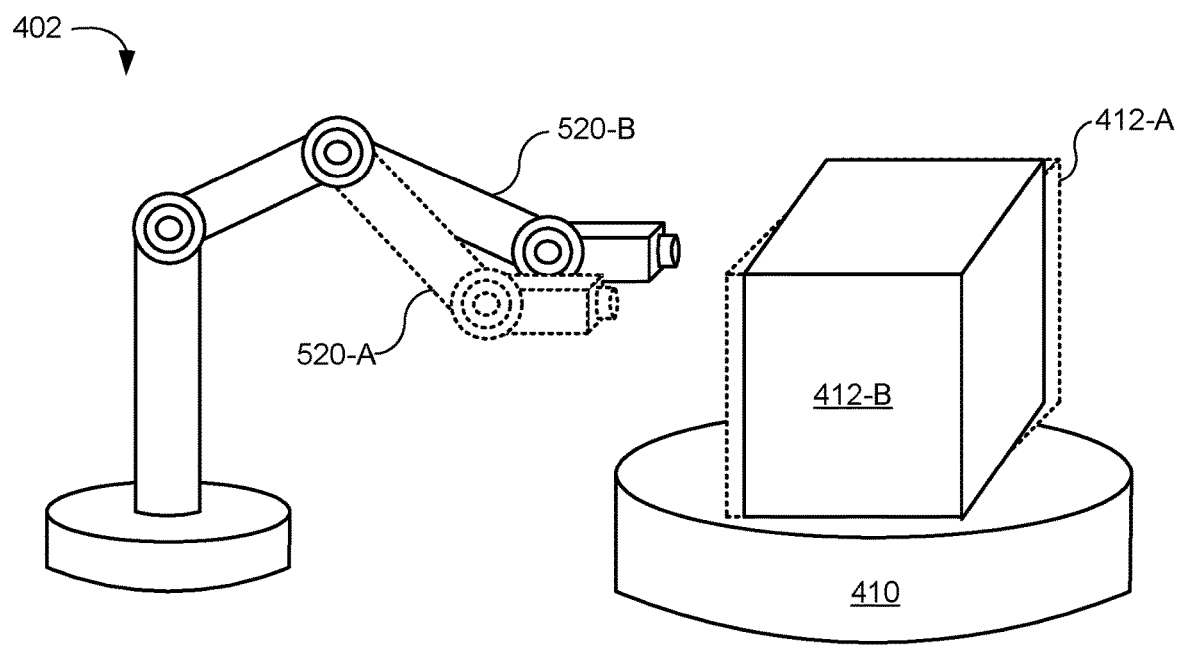
FIGS. 5C-5D show the robotic arm capturing a second image of the product and a resulting image with the defect, in accordance with some implementations.
Figure 5D:
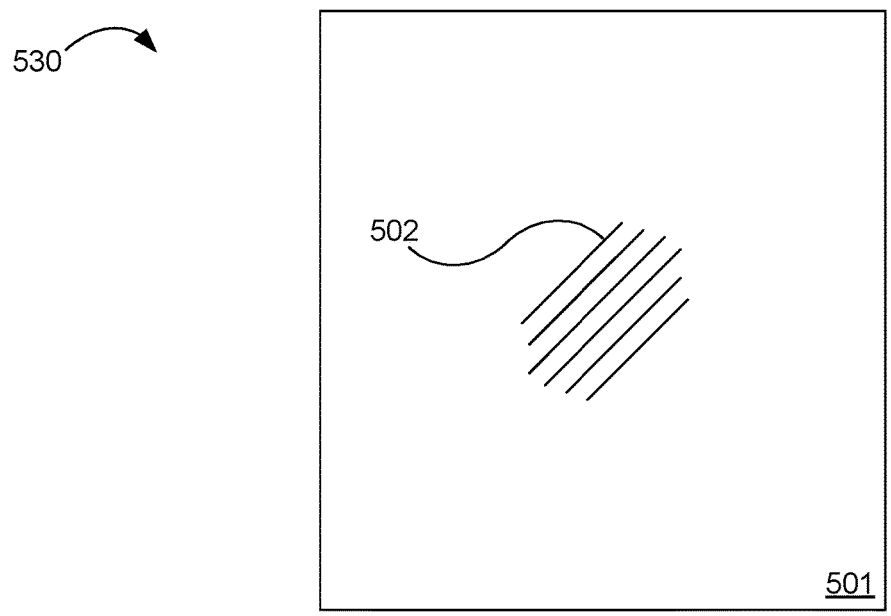

As shown in FIG. 5B, the first image 500 includes a defect 502 in piece 504-5. Accordingly, in response to identifying the defect 502, the robotic arm repositions instead to capture a second image 530 of the surface 501 of the product 512, as shown in FIGS. 5C-5D. It should be noted that a defect may span several pieces, depending on a size of the defect. For ease of discussion and illustration, the defect 502 is contained within a single piece 504-1. Additionally, in some implementations, the server system 200 (FIG. 2), processes the first image 500 instead of the robotic arm 402 (e.g., the robotic arm 402 sends the first image 500 to the server system 200 for evaluation). Moreover, in some implementations, the robotic arm 402 sends the first image 500 to the server system 200 for evaluation after identifying an abnormality in the first image 500.

FIGS. 5C-5D show the robotic arm capturing a second image 530 of the product and a result of the capturing, in accordance with some implementations.

In response to identifying the defect 502 in the first image 500, the robotic arm 402 moves (e.g., repositions) itself from a first position 520-A (dotted lines) to a second position 520-B. The robotic arm 402 in FIG. 5A is positioned at the first position 520-A, and therefore, the robotic arm 402 captures the first image 500 when positioned at the first position 520-A. In some implementations, movement between the first position 520-A and the second position 520-B is determined in accordance with the first position 520-A of the camera 408 (or one of the rotatable joints) and a relative location of the defect 502 in the first image 500. In addition, the second position 520-B is within the working space determined by the robotic arm 402, and the movement between the first position 520-A and the second position 520-B is determined in accordance with the working space. However, it should be noted that the goal of the robotic arm 402 repositioning itself is to focus the camera 408 of the defect 502 (as opposed to capturing the surface 501 in its entirety).

In some implementations, in response to identifying the defect 502 in the first image 500, the robotic arm 402 (or a component thereof such as the processor(s) 302 or a rotatable base module 334, FIG. 3) rotates the rotatable base 410. The rotatable base 410 in FIG. 5A is positioned at a first position (showing the product 412-A in a first position (dotted lines)), and therefore, the robotic arm 402 captures the first image 500 when the product 412-A is in the first position. In some implementations, the robotic arm 402 rotates the rotatable base 410 to a second position in accordance with a relative location of the defect 502 in the first image 500 (showing the product 412-B in a second position).

In some circumstances, when the robotic arm 402 repositions itself, it moves the camera 408 in multiple directions. For example, the robotic arm 402 moves the camera 408 along the Y-axis, X-axis, and Z-axis. The robotic arm 402 may move the camera 408 in multiple directions when the defect 502 is offset from the center of the first image 500 (e.g., the defect 502 in the first image 500 is offset towards an upper left corner of the surface 501). However, in some instances, when the defect 502 is not offset vertically from the center of the first image 500, the robotic arm 502 may move the camera 408 in a single direction (e.g., along the X-axis towards the surface 501 of the product 412-B). The minimal movement of the camera 408 is achieved because the rotatable base 410 repositions the defect 502 in front of the camera. Of course, if the camera 408 is no longer adjacent to the surface 501 of the product 412-B as a result of the rotation of the rotatable base 410, then the robotic arm 402 may need to take further repositioning actions.

In some implementations, the robotic arm 402 uses kinematic equations (e.g., movement algorithms 332, FIG. 3) when moving from the first position 520-A to the second position 520-B. The kinematic equations may include forward kinematic equations and/or inverse kinematic equations. Forward kinematics refers to the use of the kinematic equations of a robot to compute the position of the end-effector (e.g., a camera) from specified values for the joint parameters. In some implementations, exemplary forward kinematic equations are represented by the following equations:

|  | θ | d | a | α |
|---|---|---|---|---|
| Joint 1 | $\theta_1$ | 0 | a1 | 90° |
| Joint 2 | $\theta_2$ | 0 | a2 | 0 |
| Joint 3 | $\theta_3$ | 0 | a3 | 0 |
| Joint 4 | $\theta_4$ | 0 | a4 | 90° | where θ, d, a, and α are the Denavit-Hartenberg parameters, as known by those skilled in the art. For the robotic arm 402 shown in FIG. 4A, the following forward kinematic matrices apply:

$$A_1 = \begin{bmatrix} \cos\theta_1 & 0 & \sin\theta_1 & a_2\cos\theta_1 \\ \sin\theta_1 & 0 & -\cos\theta_1 & a_2\sin\theta_1 \\ 0 & 1 & 0 & 0 \\ 0 & 0 & 0 & 1 \end{bmatrix}$$

$$A_2 = \begin{bmatrix} \cos\theta_2 & -\sin\theta_2 & 0 & a_2\cos\theta_2 \\ \sin\theta_2 & \cos\theta_2 & 0 & a_2\sin\theta_2 \\ 0 & 0 & 1 & 0 \\ 0 & 0 & 0 & 1 \end{bmatrix}$$

$$A_3 = \begin{bmatrix} \cos\theta_3 & -\sin\theta_3 & 0 & a_3\cos\theta_3 \\ \sin\theta_3 & \cos\theta_3 & 0 & a_3\sin\theta_3 \\ 0 & 0 & 1 & 0 \\ 0 & 0 & 0 & 1 \end{bmatrix}$$

$$A_4 = \begin{bmatrix} \cos\theta_4 & 0 & \sin\theta_4 & a_4\cos\theta_4 \\ \sin\theta_4 & 0 & -\cos\theta_4 & a_4\sin\theta_4 \\ 0 & 1 & 0 & 0 \\ 0 & 0 & 0 & 1 \end{bmatrix}$$

$$A_{1234} =$$

$$A_1 A_2 A_3 A_4 = \begin{bmatrix} C_1 C_{234} & S_1 & C_1 C_{234} & C_1 C_{23}a_3 + C_1 C_2 a_2 + C_1 a_1 \\ S_1 C_{234} & -C_1 & S_1 C_{234} & S_1 C_{23}a_3 + S_1 C_2 a_2 + S_1 a_1 \\ S_{234} C_5 & -C_{234} & S_{234} S_5 & S_{23}a_3 + S_1 C_1 a_2 \\ 0 & 0 & 0 & 1 \end{bmatrix}$$

where "C"=cosine and "S"=sine.

Using the exemplary forward kinematic equations and matrices, the robotic arm 402 determines a position of an end effector (e.g., a position of the camera 408, and/or one of the rotatable joints) in a working space defined by the working space equations above.

In robotics, inverse kinematics makes use of the kinematics equations to determine the joint parameters that provide a desired position for each of a robot's end-effectors. Inverse kinematics transforms an end-effector's motion plan from a first position to a second position into joint actuator trajectories for the robot. In some implementations, exemplary inverse kinematic equations are represented by the following equations:

$$A_1 = \begin{bmatrix} n_x & o_x & a_x & p_x \\ n_y & o_y & a_y & p_y \\ n_z & o_z & a_z & p_z \\ 0 & 0 & 0 & 1 \end{bmatrix}$$

$$\theta_1 = \mathrm{atan}\left(\frac{p_x}{p_y}\right)$$

$$\theta_{234} = \mathrm{atan}(a_z, C_1 a_x + S_1 a_y)$$

$$\begin{cases} \theta_2 = \mathrm{atan}(S_3, C_3) \\ C_3 = \dfrac{(C_1 p_x + S_1 p_y - a_1)^2 + p_z^2 - a_2^2 - a_3^2}{2 a_2 a_3} \\ S_3 = \pm\sqrt{1 - C_3^2} \end{cases}$$

$$\begin{cases} \theta_3 = \mathrm{atan}(S_2, C_2) \\ S_2 = \dfrac{(a_2 + C_3 a_3) p_z - S_3 a_3 A}{(a_2 + C_3 a_3)^2 + S_3^2 a_3^2} \\ C_2 = \dfrac{(a_2 + C_3 a_3) A - S_3 a_3 p_z}{(a_2 + C_3 a_3)^2 + S_3^2 a_3^2} \\ A = p_x C_1 + p_y S_1 - a_1 \end{cases}$$

$$\theta_4 = \theta_{234} - \theta_2 - \theta_3$$

where n, o, a, and p correspond to the four joints' spatial positions in the Cartesian coordinate system.

In some implementations, the robotic arm 402 uses the inverse kinematic equations presented above to define its searching route (i.e., defining a path of the camera 408 (or one or more of the rotatable joints) from the first position 520-A to the second position 520-B. In some implementations, exemplary searching route equations are represented by the following equations for each joint of the robotic arm 402 (following equations are based on cubic interpolation):

$$\theta(t) = a_0 + a_1 t + a_2 t^2 + a_3 t^3$$

$$\dot{\theta}(t) = a_1 + 2 a_2 t + 3 a_3 t^2$$

$$\ddot{\theta}(t) = 2 a_2 + 6 a_3 t$$

$$\theta_0 = a_0$$

$$\theta_f = a_0 + a_1 t_f + a_2 t_f^2 + a_3 t_f^3$$

$$\dot{\theta}_0 = a_0$$

$$\dot{\theta}_f = a_0 + a_1 t_f + a_2 t_f^2 + a_3 t_f^3$$

$$a_0 = \theta_0$$

$$a_1 = \dot{\theta}_0$$

$$a_2 = \frac{3(\theta_f - \theta_0) - (2\dot{\theta}_0 + \dot{\theta}_f)}{t_f^3}$$

$$a_2 = \frac{3(\theta_f - \theta_0) - (2\dot{\theta}_0 + \dot{\theta}_f)}{t_f^3}$$

In our case, $\dot{\theta}_0 = 0$, $\dot{\theta}_f = 0$, so $$a_0 = \theta_0$$

$$a_1 = \dot{\theta}_0$$

$$a_2 = \frac{3(\theta_f - \theta_0)}{t_f^3} = \frac{3}{t_f^2}\Delta\theta$$

$$a_2 = -\frac{2(\theta_f - \theta_0)}{t_f^3} = -\frac{2}{t_f^3}\Delta\theta$$

where $(\theta_f - \theta_0) = \Delta\theta$, "a" and "t" are acceleration and time, respectively.

It should be noted that the equations above a merely one example of equations that can be used to control movement of the robotic arm 402. Those skilled in the art will appreciate that various other equations can be used to control movement of the robotic arm 402. Additionally, in some implementations, different equations can be used to control robotic arms 420 and 440. These equations are provided below (after the discussion of method 700).

FIGS. 6A-6B show a defect model (defect table) 600 and a defect 502 being added to the defect table 600, in accordance with some implementations. As noted above, the defect model 600 (e.g., defect model(s) 328, FIG. 3) includes defect pixels 602-A-602-N. In some implementations, a position of a defect pixel 602 in the defect model 600 corresponds to a piece (or multiple pieces) of an image being inspected (e.g., a top left corner of the defect model 600 includes pixels that correspond to a top left corner of the first image 500, FIG. 5B). Alternatively, in some implementations, a first defect model corresponds to a first piece or a first portion of the image being inspected, a second defect model corresponds to a second piece or a second portion of the image being inspected, and so on.

In some implementations, the defect pixels 602-A-602-N in the defect model 600 are previously identified defects. For example, a previously identified defect may be identified during a testing/calibration phase and/or during previous inspections (e.g., if the product 412 is a microwave oven, defects on surfaces of previously inspected microwave ovens are logged and stored in the defect model 600). Alternatively or in addition, in some implementations, a defect pixel 602 is a desired result for a piece of the product being inspected (i.e., a non-defect pixel). For example, during a testing/calibration phase, an image of a control surface of a control product is captured, and each piece of the control surface is logged and stored in the defect model 600. Moreover, this process may be repeated for several control products to form the defect model 600.

In some implementations, the defect 502 (FIG. 5B) is added to the defect model 600 after the robotic arm captures the second image 530. For example, the defect model 600 includes new defect pixel 604, which includes the defect 502. In this way, the robotic arm 402 implements machine learning to continually update the defect model 600. As such, the defect 502 may be referenced to identify defects on a subsequent product inspected by the robotic arm 402.

Figure 7:
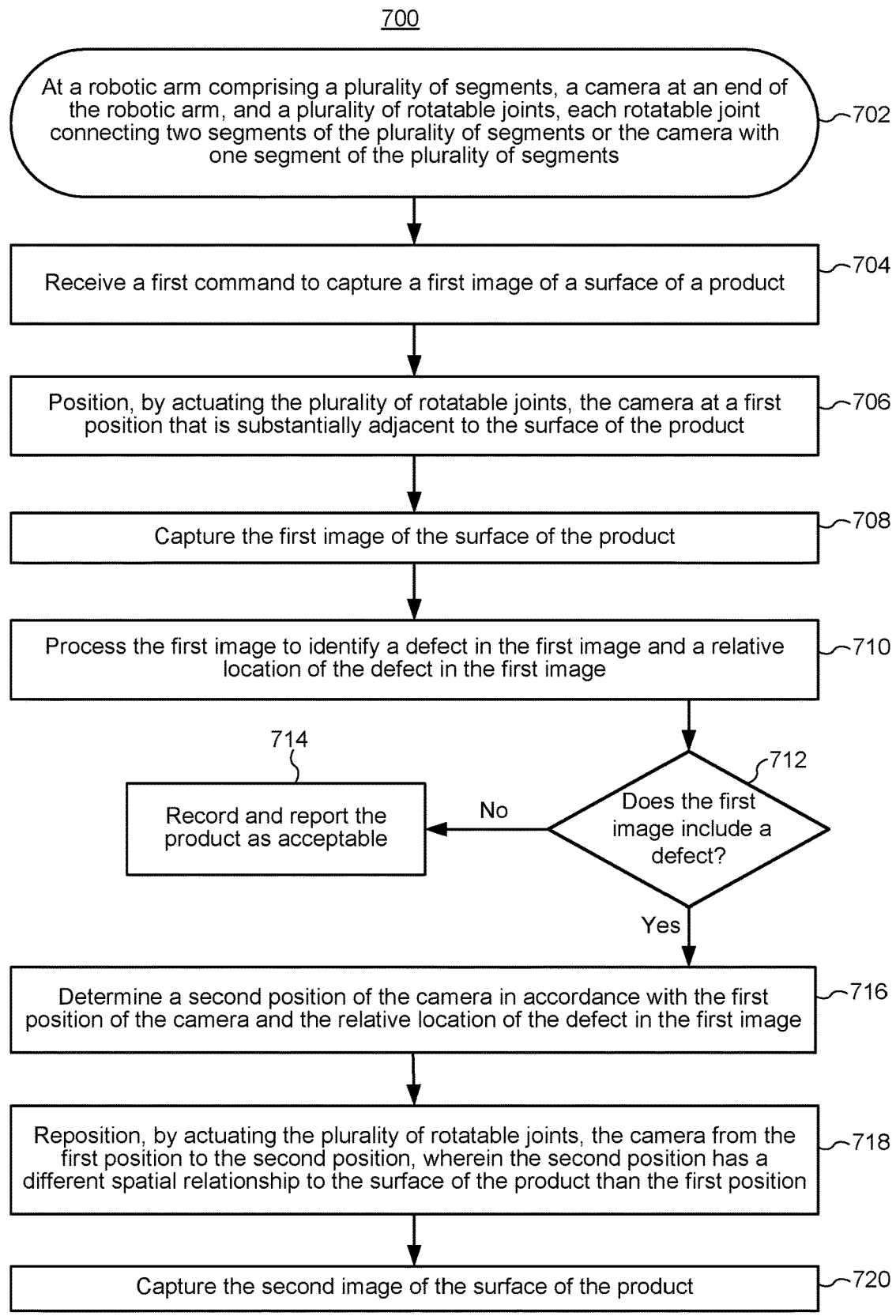
FIG. 7 is a flow diagram illustrating a method of improved quality inspection, in accordance with some implementations.

FIG. 7 is a flow diagram illustrating a method 700 of improved quality inspection on a product, in accordance with some implementations. The steps of the method 700 may be performed by a robotic arm (e.g., edge device 102, FIG. 1; robotic arm 300, FIG. 3). FIG. 7 corresponds to instructions stored in a computer memory or computer readable storage medium (e.g., memory 306 of the robotic arm 300). For example, the operations of the method 700 are performed, at least in part, by a communications module (e.g., communications module 316, FIG. 3), a positioning module (e.g., positioning module 318, FIG. 3), a capture module (e.g., capture module 320, FIG. 3), and an image inspection module (e.g., image inspection module 324, FIG. 3).

The robotic arm includes a plurality of segments (e.g., segments 404-A, 404-B, and 404-C, FIG. 4A), a camera at an end of the robotic arm (e.g., camera 408 at end of robotic arm 402, FIG. 4A), and a plurality of rotatable joints (e.g., rotatable joints 406-A-406-D, FIG. 4A), each rotatable joint connecting two segments of the plurality of segments or the camera with one segment of the plurality of segments (702). In some implementations, the plurality of rotatable joints provides the robotic arm with four degrees of freedom. Alternatively, in some implementations, the plurality of rotatable joints provides the robotic arm with five degrees of freedom. In some implementations, a first set of rotatable joints in the plurality of rotatable joints rotate about a first axis (e.g., Z-axis) and a second set of rotatable joints in the plurality of rotatable joints rotate about a second axis (e.g., Y-axis), or vice versa. In some implementations, the first set of rotatable joints is body rotatable joints (e.g., rotatable joints 406-B and 406-C, FIG. 4A) and the second set of rotatable joints is end rotatable joints (e.g., rotatable joints 406-A and 406-D, FIG. 4A). In some implementations, at least one of the rotatable joints rotates about two axes (e.g., rotatable joint 406-D, in some implementations, rotates about the Z-axis and the Y-axis, or some other combination of axes).

The method 700 includes receiving (704) a command to capture a first image of a surface (or a feature) of a product (e.g., product 412, FIG. 4A). In some implementations, the robotic arm receives the command from the server system, or some other computer (e.g., a control computer of the production line 400, FIG. 4A). As an alternative to receiving the command, in some implementations, the robotic arm recognizes the product placed in front of it. For example, the robotic arm may determine a size of the product from a video feed of the camera, and the size of the product may correspond to a product type (e.g., a product having a first size is a tea kettle and a product having a second size is a microwave oven). In response to recognizing the product, the robotic arm captures the first image of the surface of the product (discussed below). Accordingly, in these implementations, receiving the command is optional.

In some implementations, the robotic arm captures an initial image (different from the first image) of the product. Using the initial image, the robotic arm determines a working space for an end effector of the robotic arm. The working space may extend from each surface (or feature) of the product to a specific distance away from each surface (or feature) of the product. In some implementations, the end effector of the robotic arm is the camera. Alternatively or in addition, the end effector of the robotic arm is one or more of the plurality of rotatable joints. In some implementations, the working space of the end effector is determined based on a shape/size of the product (e.g., height, width, length, and volume of the product). Alternatively or in addition, in some implementations, the working space of the end effector is determined based on the camera's field of view. Determining the working space of the robotic arm is discussed in further detail above with reference to FIG. 4A.

In some implementations, in response to receiving the command (or in response to recognizing the product), the method 700 further includes positioning (706), by actuating the plurality of rotatable joints, the camera at a first position that is substantially adjacent to the surface of the product. In some implementations, the camera is centered about the surface of the product when at the first position. In some implementations, the camera is adjacent to a predetermined portion of the surface when at the first position (e.g., a defect prone portion of the surface). In some implementations, the first position is within the working space determined by the robotic arm, and the camera is the end effector of the robotic arm.

In some instances, the robotic arm positions itself in a default position after examining a previous product. The default position is a retracted position, which assures an incoming product does not damage the camera (e.g., avoid a collision between camera and the incoming product). This is especially important when a previously examined product is substantially smaller than the incoming product. As such, when retracted to the default position, positioning the camera at the first position (706) involves moving the robotic arm from the default position to the first position. The robotic arm may use the movement algorithms 332 to move the camera from the default position to the first position.

It should be noted that in some instances the camera is already at the first position, and therefore, the operation 706 may be optional, depending on the circumstances. For example, a previously examined product, such as a microwave oven, may pass inspection, and a subsequent product, which is the same model microwave oven, may then be examined, thereby not requiring movement of the camera.

In some implementations, the camera is separated from the surface by a first distance when positioned at the first position. The first distance corresponding to the working space determined by the robotic arm. Moreover, in some implementations, the camera is set at a first focal length when positioned at the first position (e.g., set to a first zoom). In some implementations, the field of view of the camera is based, at least in part, on a focal length of the camera. Accordingly, in some implementations, the robotic arm adjusts a focal length of the camera when determining the working space (e.g., zooms in or out, depending on the circumstances).

The method 700 further includes capturing (708), via the camera, the first image of the surface of the product with the camera positioned at the first position (e.g., the first position 520-A, FIG. 5C). For example, with reference to FIG. 5B, the first image 500 includes a surface 501 of the product 412.

The method 700 further includes, after capturing the first image, processing (710) the first image to identify a defect in the first image and a relative location of the defect in the first image. In some implementations, processing the first image includes comparing pieces of the first image with one or more defect models (e.g., one or more defect models 328, FIG. 3). To accomplish this, the robotic arm divides the first image into pieces (e.g., pieces 504-1-504-N, FIG. 5B) and compares at least a subset of the pieces with one or more defect models. As shown in FIG. 6A, the defect model 600 includes defect pixels 602-A-602-N. In some implementations, a defect pixel is a 1×1 pixel. Alternatively, in some implementations, a defect pixel includes multiple pixels (e.g., a 25×25 pixel, a 100×100 pixel, or some greater or lesser number of pixels). Processing an image is discussed in further detail above with reference to FIG. 5B.

In some implementations, processing the first image also includes performing an initial analysis of the first image to identify any abnormalities in the first image. The initial analysis may include comparing regions of the first image with a template (i.e., control) of the surface of the product (e.g., less demanding analysis than the comparing operation discussed above). The template of the surface includes a desired result of the surface (e.g., a previously examined surface of the product that passed quality control). If an abnormality is found, e.g., a bottom right corner of the first image differs from the template, then the robotic arm compares one or more pieces in the bottom right corner of the first image with one or more corresponding defect pixels (as discussed above). In this way, the robotic arm skips processing other pieces of the first image that do not include abnormalities, thus saving time and computing resources. For ease of discussion, an abnormality as used herein is not necessarily a defect, but is instead a deviation from a control/template. However, an abnormality can be transformed into a defect with further investigation.

In some implementations, the method 700 further includes determining (712) whether the first image includes a defect based on the processing (i.e., based on comparing the pieces of the first image with one or more defect models). In some implementations, the robotic arm determines that the first image includes a defect when a piece (or a threshold number of pieces) of the first image either: (1) matches (or partially matches) a defect pixel in the defect model, or (2) does not match (or partially match) any non-defect pixels in the defect model. In some implementations, a partially match is deemed sufficient when a threshold percentage of the defect matches the defect pixel. As discussed above, the defect model, in some implementations, includes "non-defect pixels," which are desired results for pieces of the product (e.g., pieces of the product that previously passed quality control, and were logged in a defect model 328, FIG. 3). Determining that an image incudes a defect is discussed in further detail above with reference to FIG. 5B.

In some implementations, the robotic arm creates a local binary pattern (LBP) to determine whether the first image includes a defect. To create the LBP, a value is assigned to a piece based on the processing (710). For example, a first value is assigned to the piece when the piece directly matches a defect pixel (e.g., a 90% match) and a second value, less than the first value, is assigned to the piece when the piece partially matches a defect pixel (e.g., 60% match) (values may also assigned using non-defect pixels). Moreover, the value of the piece is compared to values of neighboring pieces (e.g., any given piece has eight neighboring pieces). Continuing, if the value of the piece is greater than a neighboring piece's value, then the piece is assigned a "1," and if the value of the piece is less than a neighboring piece's value, then the piece is assigned a "0." After the comparing, a total metric is assigned to the piece. In some implementations, the metric is an eight digit binary number with each digit corresponding to one of the eight comparisons. The process described above is repeated for multiple pieces (or each piece) in the first image, and a chart (e.g., a histogram) is created to illustrate the results. The chart includes a frequency of each binary number occurring. A region (e.g., a first location) of the histogram having a first binary number (or an average first binary number) may indicate that that region includes a defect and a different region (e.g., a second location) of the histogram having a second binary number (or an average second binary number) may indicate that that region does not include a defect. The histogram may be an N-number dimensional feature vector, and in some implementations, the histogram is normalized. In such implementations, a feature vector is established for the first image.

In some implementations, a support vector machine (SVM) is also used to determine that the first image includes a defect. The SVM is a supervised learning model in machine learning with associated learning algorithms that analyze data used for classification and regression analysis. For example, given a set of training examples, each marked as belonging to one or the other of two categories, an SVM training algorithm builds a binary classifier that assigns new examples to one category or the other. An SVM model is a representation of the examples as points in space, mapped so that the examples of the separate categories are divided by a clear gap that is as wide as possible. New examples are then mapped into that same space and predicted to belong to a category based on which side of the gap they fall. In some implementations, the SVM determines that the first image includes a defect using the LBP discussed above.

In response to determining that the first image does not include a defect (712—No), the method 700 further includes recording and reporting (714) the product as acceptable. Alternatively, in response to determining that the first image includes a defect (712—Yes), the method 700 further includes determining (716) a second position of the camera in accordance with the first position of the camera and the relative location of the defect in the first image. It should be noted that, when determining that the first image includes a defect, the robotic arm may be determining that the first image likely has a defect. As such, as is discussed below, the robotic arm captures a second image of the surface to verify that the identified defect is actually a defect.

The method 700 further includes repositioning (718), by actuating the plurality of rotatable joints, the camera from the first position to the second position. The second position has a different spatial relationship to the surface of the product than the first position. For example, the camera is separated from the surface by a second distance when repositioned at the second position, and the second distance is less than the first distance. Moreover, in some implementations, the camera is set at a second focal length when repositioned at the second position, and the second focal length is greater than the first focal length (e.g., set to a second zoom). The goal of the robotic arm repositioning itself is to focus the camera of the defect (as opposed to capturing the surface in its entirety). For example, as shown in FIG. 5D, the defect is magnified in a center portion of the second image 530. In this way, the robotic arm can verify that the identified defect is actually a defect The method 700 further includes capturing (720), via the camera, the second image of the surface of the product with the camera positioned at the second position. In response to capturing the second image, in some implementations, the robotic arm verifies that the identified defect is actually a defect. To verify the defect, the robotic arm again compares the defect with defect pixels (and/or non-defect pixels) in the defect model. This comparison operation, however, is more granular relative to the first image's comparison operation. The robotic may determine that the defect corresponds to an already identified defect (e.g., a defect caused by a tool). Alternatively, the robotic may determine that the defect does not correspond to any already identified defect, but it is nevertheless a defect. In either case, the robotic arm may generate a report and provide the report to the appropriate party (e.g., a processing engineer responsible for a specific part of the manufacturing process). After verifying the defect, in some implementations, the method 700 includes recording and reporting the product as unacceptable.

Moreover, in some implementations, the method 700 further includes updating the defect model to include the defect. For example, with reference to FIG. 6B, new defect pixel 604, which includes the defect 502, is added to the defect model 610. In some implementations, the defect is added to the defect model after step 712—Yes. Alternatively, in some implementations, the defect is added to the defect model after verifying the defect.

In some implementations, however, the robotic arm cannot verify the defect. In such cases, the method 700 includes recording and reporting the product as acceptable. In these circumstances, the robotic arm may update the defect model to include the non-verified defect as being an acceptable abnormality (i.e., a non-defect pixel).

In some implementations, the product is positioned on a rotatable base (e.g., rotatable base 311, FIG. 3; rotatable base 410, FIG. 4A). Further, in some implementations, the method 700 includes rotating the rotatable base in accordance with the relative location of the defect in the first image after capturing the first image. The second image is then captured after rotating the rotatable base. For example, the robotic arm (or a component thereof such as processors 302 or rotatable base module 334, FIG. 3) controls the rotatable base and rotates the rotatable base so that the defect is positioned in front of the camera. This configuration minimizes a degree of movement required by the robotic arm because the defect essentially comes to the camera instead of the camera going to the defect. As such, time and resources are conserved when the rotatable base is included. Moreover, a length of each segment in the plurality of segments can be substantially reduced because the robotic arm does not have to reach distant lateral surfaces of the product. At most, the robotic arm is required to reach a top surface of the product, assuming that the top surface needs inspecting.

In some implementations, prior to capturing the first image, the method 700 further includes determining a size of the product, and based on the determined size, the robotic arm determines it working space. For example, the robotic arm, when positioned at the default position, detects the product in front of it, and determines the size of the product using an image captured by the camera and the camera's position. In some implementations, in order to determine the size of the product, the robotic arm captures an initial image of the product and determines the size of the product from the initial image and the position of the camera capturing the initial image. Alternatively, in some implementations, the robotic arm evaluates the product based on a video feed from the camera.

In some implementations, the method 700 further includes repositioning, by actuating the plurality of rotatable joints, the camera at one or more additional positions, where each additional position is substantially adjacent to a respective additional surface (or an additional feature) of the product. For example, with reference to FIGS. 4B-4C, the robotic arms 420 and 440 reach distant lateral surfaces of the product 412. However, in those implementations involving the rotatable base (e.g., FIG. 4A), the robotic arm can leverage the rotatable base to rotate the product so that each respective additional surface of the product is positioned in front of the camera. Again, this arrangement results in the additional surfaces coming to the camera instead of the camera going to the defect. In this way, time and resources are conserved.

In some implementations, the method 700 further includes capturing, via the camera, an additional image of each respective additional surface of the product with the camera positioned at the one or more additional positions. Each additional image is processed in the same manner as discussed above.

The following equations relate to the robotic arms 420 and 440, discussed above with reference to FIGS. 4B-4C.

In some implementations, the robotic arm 420 uses kinematic equations (e.g., movement algorithms 332, FIG. 3) when moving from one position to another. The kinematic equations may include forward kinematic equations and/or inverse kinematic equations. In some implementations, exemplary forward kinematic equations are represented by the following equations:

|         | θ          | d | a     | α    |
|---------|------------|---|-------|------|
| Joint 1 | $\theta_1$ | 0 | $a_1$ | 90°  |
| Joint 2 | $\theta_2$ | 0 | $a_2$ | 0    |
| Joint 3 | $\theta_3$ | 0 | $a_3$ | 0    |
| Joint 4 | $\theta_4$ | 0 | 0     | 0    |
| Joint 5 | $\theta_5$ | 0 | 0     | 90°  | where θ, d, a, and α are the Denavit-Hartenberg parameters, as known by those skilled in the art. For the robotic arm 420 shown in FIG. 4B, the following forward kinematic matrices apply:

$$A_1 = \begin{bmatrix} \cos\theta_1 & 0 & \sin\theta_1 & a_2\cos\theta_1 \\ \sin\theta_1 & 0 & -\cos\theta_1 & a_2\sin\theta_1 \\ 0 & 1 & 0 & 0 \\ 0 & 0 & 0 & 1 \end{bmatrix}$$

$$A_2 = \begin{bmatrix} \cos\theta_2 & -\sin\theta_2 & 0 & a_2\cos\theta_2 \\ \sin\theta_2 & \cos\theta_2 & 0 & a_2\sin\theta_2 \\ 0 & 0 & 1 & 0 \\ 0 & 0 & 0 & 1 \end{bmatrix}$$

$$A_3 = \begin{bmatrix} \cos\theta_3 & -\sin\theta_3 & 0 & a_3\cos\theta_3 \\ \sin\theta_3 & \cos\theta_3 & 0 & a_3\sin\theta_3 \\ 0 & 0 & 1 & 0 \\ 0 & 0 & 0 & 1 \end{bmatrix}$$

$$A_4 = \begin{bmatrix} \cos\theta_4 & 0 & \sin\theta_4 & a_4\cos\theta_4 \\ \sin\theta_4 & 0 & -\cos\theta_4 & a_4\sin\theta_4 \\ 0 & 1 & 0 & 0 \\ 0 & 0 & 0 & 1 \end{bmatrix}$$

$$A_5 = \begin{bmatrix} \cos\theta_5 & 0 & \sin\theta_5 & a_5\cos\theta_5 \\ \sin\theta_5 & 0 & -\cos\theta_5 & a_5\sin\theta_5 \\ 0 & 1 & 0 & 0 \\ 0 & 0 & 0 & 1 \end{bmatrix}$$

$$A_{12345} =$$

$$\begin{bmatrix} C_1C_{234}C_5 & C_1S_{234} & C_1C_{234}S_5 - S_1C_5 & C_1C_{23}a_3 + C_1C_2a_2 + C_1a_1 \\ S_1C_{234}C_5 & S_1S_{234} & S_1C_{234}S_5 + C_1C_5 & S_1C_{23}a_3 + S_1C_2a_2 + S_1a_1 \\ S_{234}C_5 & -C_{234} & S_{234}S_5 & S_{23}a_3 + S_1C_1a_2 \\ 0 & 0 & 0 & 1 \end{bmatrix}$$

where "C"=cosine and "S"=sine.

In some implementations, exemplary inverse kinematic equations for the robotic arm 420 are represented by the following equations:

$$= \begin{bmatrix} n_x & o_x & a_x & p_x \\ n_y & o_y & a_y & p_y \\ n_z & o_z & a_z & p_z \\ 0 & 0 & 0 & 1 \end{bmatrix}$$

-continued

And $$\theta_1 = \operatorname{atan}\left(\frac{p_x}{p_y}\right)$$

$$\theta_{234} = \operatorname{atan}(a_z, C_1 a_x + S_1 a_y)$$

$$\begin{cases} \theta_2 = \operatorname{atan}(S_3, C_3) \\ C_3 = \dfrac{(C_1 p_x + S_1 p_y - a_1)^2 + p_z^2 - a_2^2 - a_3^2}{2 a_2 a_3} \\ S_3 = \pm\sqrt{1 - C_3^2} \end{cases}$$

$$\begin{cases} \theta_3 = \operatorname{atan}(S_2, C_2) \\ S_2 = \dfrac{(a_2 + C_3 a_3) p_z - S_3 a_3 A}{(a_2 + C_3 a_3)^2 + S_3^2 a_3^2} \\ C_2 = \dfrac{(a_2 + C_3 a_3) A - S_3 a_3 p_z}{(a_2 + C_3 a_3)^2 + S_3^2 a_3^2} \\ A = p_x C_1 + p_y S_1 - a_1 \end{cases}$$

$$\theta_4 = \theta_{234} - \theta_2 - \theta_3$$

$$\begin{cases} \theta_5 = \operatorname{atan}(S_5, C_5) \\ S_5 = C_1 C_{234} a_x + S_1 C_{234} a_y + S_{234} a_z \\ C_2 = C_1 a_y + s_1 a_x \end{cases}$$

In some implementations, the robotic arm 420 uses the inverse kinematic equations presented above to define its searching route (i.e., defining a path of the camera 428 (or one or more of the rotatable joints) from a first position to a second position). In some implementations, exemplary searching route equations are represented by the following equations (following equations are based on cubic interpolation):

$$\theta(t) = a_0 + a_1 t + a_2 t^2 + a_3 t^3$$

$$\dot{\theta}(t) = a_1 + 2 a_2 t + 3 a_3 t^2$$

$$\ddot{\theta}(t) = 2 a_2 + 6 a_3 t$$

$$\theta_0 = a_0$$

$$\theta_f = a_0 + a_1 t_f + a_2 t_f^2 + a_3 t_f^3$$

$$\dot{\theta}_0 = a_1$$

$$\dot{\theta}_f = a_0 + a_1 t_f + a_2 t_f^2 + a_3 t_f^3$$

$$a_0 = \theta_0$$

$$a_1 = \dot{\theta}_0$$

$$a_2 = \frac{3(\theta_f - \theta_0) - (2\dot{\theta}_0 + \dot{\theta}_f)}{t_f^3}$$

$$a_2 = \frac{3(\theta_f - \theta_0) - (2\dot{\theta}_0 + \dot{\theta}_f)}{t_f^3}$$

In our case, $$a_0 = \theta_0$$

$$a_1 = \dot{\theta}_0$$

$$a_2 = \frac{3(\theta_f - \theta_0) - (2\dot{\theta}_0 + \dot{\theta}_f)}{t_f^3}$$

-continued $$a_2 = \frac{3(\theta_f - \theta_0) - (2\dot{\theta}_0 + \dot{\theta}_f)}{t_f^3}$$

In some implementations, the robotic arm 440 uses kinematic equations (e.g., movement algorithms 332, FIG. 3) when moving from one position to another. The kinematic equations may include forward kinematic equations and/or inverse kinematic equations. In some implementations, exemplary forward kinematic equations are represented by the following equations:

|  | θ | d | a | α |
|---|---|---|---|---|
| Joint 1 | $\theta_1$ | 0 | $a_1$ | 90° |
| Joint 2 | $\theta_2$ | 0 | $a_2$ | 0 |
| Joint 3 | $\theta_3$ | 0 | $a_3$ | 0 |
| Joint 4 | $\theta_4$ | 0 | 0 | 90° | where θ, d, a, and α are the Denavit-Hartenberg parameters, as known by those skilled in the art. For the robotic arm 440 shown in FIG. 4C, the following forward kinematic matrices apply:

$$A_1 = \begin{bmatrix} \cos\theta_1 & 0 & \sin\theta_1 & a_2 \cos\theta_1 \\ \sin\theta_1 & 0 & -\cos\theta_1 & a_2 \sin\theta_1 \\ 0 & 1 & 0 & 0 \\ 0 & 0 & 0 & 1 \end{bmatrix}$$

$$A_2 = \begin{bmatrix} \cos\theta_2 & -\sin\theta_2 & 0 & a_2 \cos\theta_2 \\ \sin\theta_2 & \cos\theta_2 & 0 & a_2 \sin\theta_2 \\ 0 & 0 & 1 & 0 \\ 0 & 0 & 0 & 1 \end{bmatrix}$$

$$A_3 = \begin{bmatrix} \cos\theta_3 & -\sin\theta_3 & 0 & a_3 \cos\theta_3 \\ \sin\theta_3 & \cos\theta_3 & 0 & a_3 \sin\theta_3 \\ 0 & 0 & 1 & 0 \\ 0 & 0 & 0 & 1 \end{bmatrix}$$

$$A_4 = \begin{bmatrix} \cos\theta_4 & 0 & \sin\theta_4 & a_4 \cos\theta_4 \\ \sin\theta_4 & 0 & -\cos\theta_4 & a_4 \sin\theta_4 \\ 0 & 1 & 0 & 0 \\ 0 & 0 & 0 & 1 \end{bmatrix}$$

$$A_{1234} = \begin{bmatrix} C_1 C_{234} & S_1 & C_1 C_{234} & C_1 C_{23} a_3 + C_1 C_2 a_2 + C_1 a_1 \\ S_1 C_{234} & -C_1 & S_1 C_{234} & S_1 C_{23} a_3 + S_1 C_2 a_2 + S_1 a_1 \\ S_{234} C_5 & -C_{234} & S_{234} S_5 & S_{23} a_3 + S_1 C_1 a_2 \\ 0 & 0 & 0 & 1 \end{bmatrix}$$

where "C"=cosine and "S"=sine.

In some implementations, exemplary inverse kinematic equations for the robotic arm 440 are represented by the following equations:

$$= \begin{bmatrix} n_x & o_x & a_x & p_x \\ n_y & o_y & a_y & p_y \\ n_z & o_z & a_z & p_z \\ 0 & 0 & 0 & 1 \end{bmatrix}$$

-continued

And $$\theta_1 = \operatorname{atan}\left(\frac{p_x}{p_y}\right)$$

$$\theta_{234} = \operatorname{atan}(a_z, C_1 a_x + S_1 a_y)$$

$$\begin{cases} \theta_2 = \operatorname{atan}(S_3, C_3) \\ C_3 = \dfrac{(C_1 p_x + S_1 p_y - a_1)^2 + p_z^2 - a_2^2 - a_3^2}{2 a_2 a_3} \\ S_3 = \pm\sqrt{1 - C_3^2} \end{cases}$$

$$\begin{cases} \theta_3 = \operatorname{atan}(S_2, C_2) \\ S_2 = \dfrac{(a_2 + C_3 a_3) p_z - S_3 a_3 A}{(a_2 + C_3 a_3)^2 + S_3^2 a_3^2} \\ C_2 = \dfrac{(a_2 + C_3 a_3) A - S_3 a_3 p_z}{(a_2 + C_3 a_3)^2 + S_3^2 a_3^2} \\ A = p_x C_1 + p_y S_1 - a_1 \end{cases}$$

$$\theta_4 = \theta_{234} - \theta_2 - \theta_3$$

In some implementations, the robotic arm 440 uses the inverse kinematic equations presented above to define its searching route (i.e., defining a path of the camera 448 (or one or more of the rotatable joints) from a first position to a second position). In some implementations, exemplary searching route equations are represented by the following equations (following equations are based on cubic interpolation):

$$\theta(t) = \alpha_0 + \alpha_1 t + \alpha_2 t^2 + \alpha_3 t^3$$

$$\dot{\theta}(t) = \alpha_1 + 2\alpha_2 t + 3\alpha_3 t$$

$$\ddot{\theta}(t) = 2\alpha_2 + 6\alpha_3 t$$

$$\theta_0 = \alpha_0$$

$$\theta_f = \alpha + \alpha_1 t_f + \alpha_2 t_f^2 + \alpha_3 t_f^3$$

$$\dot{\theta}_0 = \alpha_1$$

$$\dot{\theta}_f = \alpha + \alpha_1 t_f + \alpha_2 t_f^2 + \alpha_3 t_f^3$$

$$a_0 = \theta_0$$

$$a_1 = \dot{\theta}_0$$

$$a_2 = \frac{3(\theta_f - \theta_0) - (2\dot{\theta}_0 + \dot{\theta}_f)}{t_f^3}$$

$$a_2 = \frac{3(\theta_f - \theta_0) - (2\dot{\theta}_0 + \dot{\theta}_f)}{t_f^3}$$

In our case, $$a_0 = \theta_0$$

$$a_1 = \dot{\theta}_0$$

$$a_2 = \frac{3(\theta_f - \theta_0) - (2\dot{\theta}_0 + \dot{\theta}_f)}{t_f^3}$$

$$a_2 = \frac{3(\theta_f - \theta_0) - (2\dot{\theta}_0 + \dot{\theta}_f)}{t_f^3}$$

Although some of various drawings illustrate a number of logical stages in a particular order, stages which are not order dependent may be reordered and other stages may be combined or broken out. While some reordering or other groupings are specifically mentioned, others will be obvious to those of ordinary skill in the art, so the ordering and groupings presented herein are not an exhaustive list of alternatives. Moreover, it should be recognized that the stages could be implemented in hardware, firmware, software or any combination thereof.

The foregoing description, for purpose of explanation, has been described with reference to specific implementations. However, the illustrative discussions above are not intended to be exhaustive or to limit the scope of the claims to the precise forms disclosed. Many modifications and variations are possible in view of the above teachings. The implementations were chosen in order to best explain the principles underlying the claims and their practical applications, to thereby enable others skilled in the art to best use the implementations with various modifications as are suited to the particular uses contemplated.

What is claimed is:

1. A robotic arm comprising:
   a plurality of segments, including a distal segment with a distal end;
   a camera at the distal end of the distal segment;
   a plurality of joints connecting two segments of the plurality of segments;
   one or more processors; and
   memory storing one or more programs for execution by the one or more processors, the one or more programs including instructions for:
   inspecting, via the camera, a surface of a product with the camera positioned at a first position;
   based on the inspecting, identifying: (i) an area of interest on the surface of the product, and (ii) a relative location of the area of interest on the surface, wherein identifying the area of interest on the surface of the product and the relative location of the area of interest on the surface comprises:
   sending image data, gathered by inspecting the surface of the product with the camera positioned at the first position, to another device that evaluates the image data for potential defects; and
   receiving, from the other device, an indication of the area of interest on the surface of the product and the relative location of the area of interest on the surface;
   positioning, based on the relative location of the area of interest on the surface, the camera at a second position; and
   inspecting, via the camera, the area of interest on the surface of the product with the camera positioned at the second position, wherein inspecting the area of interest comprises inspecting a subset of the surface of the product.

2. The robotic arm of claim 1, wherein identifying the area of interest on the surface of the product comprises:
   comparing one or more regions of the product with a template; and based on the comparing, determining that at least one region of the one or more regions differs from the template.

3. The robotic arm of claim 1, wherein:
inspecting the surface of the product with the camera positioned at the first position comprises capturing an image; and
identifying the area of interest on the surface of the product comprises:
comparing one or more pixels of the image with a defect model, the defect model comprising a plurality of defect pixels; and
based on the comparison, determining that a threshold number of pixels of the one or more pixels substantially match one or more defect pixels of the plurality of defect pixels.

4. The robotic arm of claim 1, further comprising:
based on the inspecting of the subset of the surface of the product with the camera positioned at the second position, determining whether the area of interest includes a defect; and
in response to determining that the area of interest includes a defect, reporting the product as unacceptable.

5. The robotic arm of claim 4, wherein the one or more programs further include instructions for:
inspecting the area of interest with the camera positioned at the second position comprises capturing an image; and
determining whether the area of interest includes the defect comprises:
comparing one or more pixels of the image with a defect model, the defect model comprising a plurality of defect pixels; and
based on the comparison, determining that a threshold number of pixels of the one or more pixels substantially match one or more defect pixels of the plurality of defect pixels.

6. The robotic arm of claim 1, wherein:
the product is positioned on a rotatable base;
the one or more programs further include instructions for rotating the rotatable base in accordance with the relative location of the area of interest; and
inspecting the area of interest is performed after rotating the rotatable base.

7. The robotic arm of claim 1, wherein the first position is different from the second position.

8. The robotic arm of claim 7, wherein positioning the camera at the second position comprises repositioning, by actuating one or more joints of the plurality of joints, the camera from the first position to the second position.

9. The robotic arm of claim 1, wherein:
the camera is separated from the surface by a first distance when positioned at the first position;
the camera is separated from the surface by a second distance when positioned at the second position; and
the second distance is less than the first distance.

10. The robotic arm of claim 1, wherein:
the camera is set at a first zoom when positioned at the first position;
the camera is set at a second zoom when positioned at the second position; and
the second zoom is greater than the first zoom.

11. The robotic arm of claim 1, wherein:
one or more first joints of the plurality of joints rotate about a first axis; and
one or more second joints of the plurality of joints rotate about a second axis different from the first axis.

12. The robotic arm of claim 1, wherein one of the plurality of joints connects the camera with the distal segment.

13. The robotic arm of claim 1, wherein the plurality of joints is a plurality of rotatable joints.

14. A method comprising:
at a robotic arm comprising a plurality of segments, a camera at an end of the robotic arm, and a plurality of joints connecting two segments of the plurality of segments:
inspecting, via the camera, a surface of a product with the camera positioned at a first position;
based on the inspecting, identifying: (i) an area of interest on the surface of the product, and (ii) a relative location of the area of interest on the surface, wherein identifying the area of interest on the surface of the product and the relative location of the area of interest on the surface comprises:
sending image data, gathered by inspecting the surface of the product with the camera positioned at the first position, to another device that evaluates the image data for potential defects; and
receiving, from the other device, an indication of the area of interest on the surface of the product and the relative location of the area of interest on the surface;
positioning, based on the relative location of the area of interest on the surface, the camera at a second position; and
inspecting, via the camera, the area of interest on the surface of the product with the camera positioned at the second position, wherein inspecting the area of interest comprises inspecting a subset of the surface of the product.

15. The method of claim 14, further comprising:
based on the inspecting of the subset of the surface of the product with the camera positioned at the second position, determining whether the area of interest includes a defect; and
in response to determining that the area of interest includes a defect, reporting the product as unacceptable.

16. The method of claim 15, wherein:
inspecting the area of interest with the camera positioned at the second position comprises capturing an image; and
determining whether the area of interest includes the defect comprises:
comparing one or more pixels of the image with a defect model, the defect model comprising a plurality of defect pixels; and
based on the comparison, determining that a threshold number of pixels of the one or more pixels substantially match one or more defect pixels of the plurality of defect pixels.

17. A non-transitory computer-readable storage medium, storing one or more programs configured for execution by one or more processors of a robotic arm having a plurality of segments, a camera at an end of the robotic arm, and a plurality of joints connecting two segments of the plurality of segments, the one or more programs including instructions, which when executed by the one or more processors, cause the robotic arm to:
inspect, via the camera, a surface of a product with the camera positioned at a first position;

based on the inspecting, identify: (i) an area of interest on the surface of the product, and (ii) a relative location of the area of interest on the surface, wherein identifying the area of interest on the surface of the product and the relative location of the area of interest on the surface comprises:
  sending image data, gathered by inspecting the surface of the product with the camera positioned at the first position, to another device that evaluates the image data for potential defects; and
  receiving, from the other device, an indication of the area of interest on the surface of the product and the relative location of the area of interest on the surface;
position, based on the relative location of the area of interest on the surface, the camera at a second position; and
inspect, via the camera, the area of interest on the surface of the product with the camera positioned at the second position, wherein inspecting the area of interest comprises inspecting a subset of the surface of the product.

18. The non-transitory computer-readable storage medium of claim 17, wherein the one or more programs further include instructions, which when executed by the one or more processors, cause the robotic arm to:
  determine whether the area of interest includes a defect, based on the inspecting of the subset of the surface of the product with the camera positioned at the second position; and
  report the product as unacceptable, in response to determining that the area of interest includes a defect.

19. The non-transitory computer-readable storage medium of claim 18, wherein:
  inspecting the area of interest with the camera positioned at the second position comprises capturing an image; and
  determining whether the area of interest includes the defect comprises:
    comparing one or more pixels of the image with a defect model, the defect model comprising a plurality of defect pixels; and
    based on the comparison, determining that a threshold number of pixels of the one or more pixels substantially match one or more defect pixels of the plurality of defect pixels.

* * * * *